United States Patent
Fan et al.

(10) Patent No.: US 9,086,370 B2
(45) Date of Patent: *Jul. 21, 2015

(54) METHOD FOR NANOPARTICLE ELECTROGENERATED CHEMILUMINESCENCE AMPLIFICATION

(71) Applicant: Board of Regents, the University of Texas System, Austin, TX (US)

(72) Inventors: Fu-Ren F. Fan, Austin, TX (US); Allen J. Bard, Austin, TX (US); Xiaoying Xiao, Austin, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/056,849

(22) Filed: Oct. 17, 2013

(65) Prior Publication Data
US 2014/0042037 A1 Feb. 13, 2014

Related U.S. Application Data

(62) Division of application No. 12/936,675, filed as application No. PCT/US2009/002160 on Apr. 7, 2009, now Pat. No. 8,586,378.

(60) Provisional application No. 61/123,780, filed on Apr. 11, 2008, provisional application No. 61/123,943, filed on Apr. 11, 2008, provisional application No. 61/124,935, filed on Apr. 21, 2008.

(51) Int. Cl.
*G01N 15/10* (2006.01)
*G01N 27/26* (2006.01)
(Continued)

(52) U.S. Cl.
CPC ........ *G01N 27/26* (2013.01); *G01N 15/10* (2013.01); *G01N 15/14* (2013.01); *G01N 21/76* (2013.01); *G01N 33/542* (2013.01); *G01N 33/54373* (2013.01); *G01N 2458/30* (2013.01)

(58) Field of Classification Search
None
See application file for complete search history.

(56) References Cited

U.S. PATENT DOCUMENTS 5,061,445 A  10/1991  Zoski et al.
5,093,268 A   3/1992  Leventis et al.
(Continued)

FOREIGN PATENT DOCUMENTS

CA       1339465       9/1997
WO    WO 87/06706    11/1987
(Continued)

OTHER PUBLICATIONS

Choi, J.-P. "Electrogenerated Chemiluminescence with Amine and Benzoyl Peroxide Coreactants: Reactivity and Reaction Mechanism Studies," Dissertation at The University of Texas at Austin, Dec. 2003; available from ProQuest in 2004.*

(Continued)

*Primary Examiner* — Yelena G Gakh
*Assistant Examiner* — Michelle Adams
(74) *Attorney, Agent, or Firm* — Foley & Lardner LLP

(57) ABSTRACT

Methods and devices for signal amplification and/or analyzing a chemical analyte using an electrochemical cell containing colloidal suspension of conductive or redox active nanoparticles in a liquid sample are provided. The liquid sample includes a plurality of electrogenerated chemiluminescent (ECL) moieties and one or more chemical analytes. The colloidal suspension of nanoparticles in the liquid sample are in contact with one or more electrodes of the electrochemical cell. The methods and devices may also employ an optical detection system, which is capable of measuring one or more transient optical properties resulting from redox reactions of the ECL moieties catalyzed by interaction of the nanoparticles with one of the electrodes.

20 Claims, 16 Drawing Sheets

(51) Int. Cl.
*G01N 21/76* (2006.01)
*G01N 15/14* (2006.01)
*G01N 33/542* (2006.01)
*G01N 33/543* (2006.01)

(56) References Cited

U.S. PATENT DOCUMENTS

| | | |
|---|---|---|
| 5,238,808 A | 8/1993 | Bard et al. |
| 5,296,191 A | 3/1994 | Hall et al. |
| 5,324,457 A | 6/1994 | Zhang et al. |
| 5,369,036 A | 11/1994 | Mercolino et al. |
| 5,500,188 A | 3/1996 | Hafeman et al. |
| 5,527,710 A | 6/1996 | Nacamulli et al. |
| 5,571,401 A | 11/1996 | Lewis et al. |
| 5,610,075 A | 3/1997 | Stahl-Rees |
| 5,679,519 A | 10/1997 | Opandy |
| 5,686,244 A | 11/1997 | Gudibande et al. |
| 5,700,427 A | 12/1997 | Ghaed et al. |
| 5,705,402 A | 1/1998 | Leland et al. |
| 5,714,089 A | 2/1998 | Bard et al. |
| 5,731,147 A | 3/1998 | Bard et al. |
| 5,786,141 A | 7/1998 | Bard et al. |
| 5,792,621 A | 8/1998 | Verostko et al. |
| 5,798,083 A | 8/1998 | Massey et al. |
| 5,804,400 A | 9/1998 | Martin et al. |
| 5,858,676 A | 1/1999 | Yang et al. |
| 5,866,434 A | 2/1999 | Massey et al. |
| 5,945,344 A | 8/1999 | Hayes et al. |
| 6,087,476 A | 7/2000 | Kenten et al. |
| 6,096,500 A | 8/2000 | Oprandy et al. |
| 6,120,986 A | 9/2000 | Martin |
| 6,127,516 A | 10/2000 | Bard et al. |
| 6,132,648 A | 10/2000 | Zhang et al. |
| 6,133,043 A | 10/2000 | Talley et al. |
| 6,136,233 A | 10/2000 | Jameison et al. |
| 6,136,268 A | 10/2000 | Ala-Kleme et al. |
| 6,140,045 A | 10/2000 | Wohlstadter et al. |
| 6,140,138 A | 10/2000 | Bard et al. |
| 6,146,838 A | 11/2000 | Williams et al. |
| 6,165,708 A | 12/2000 | Liang et al. |
| 6,200,531 B1 | 3/2001 | Lijestand et al. |
| 6,312,896 B1 | 11/2001 | Heroux et al. |
| 6,316,607 B1 | 11/2001 | Massey et al. |
| 6,319,670 B1 | 11/2001 | Sigal et al. |
| 6,325,973 B1 | 12/2001 | Leland et al. |
| 6,468,741 B1 | 10/2002 | Massey et al. |
| 6,479,233 B1 | 11/2002 | Bard et al. |
| 6,517,777 B2 | 2/2003 | Liljestrand et al. |
| 6,537,498 B1 | 3/2003 | Lewis et al. |
| 6,613,583 B1 | 9/2003 | Richter et al. |
| 6,635,418 B2 | 10/2003 | Heroux et al. |
| 6,702,986 B1 | 3/2004 | Leland et al. |
| 6,808,939 B2 | 10/2004 | Sigal et al. |
| 6,846,629 B2 | 1/2005 | Sigal et al. |
| 6,852,502 B1 | 2/2005 | Martin |
| 6,881,536 B1 | 4/2005 | Shah et al. |
| 6,890,712 B1 | 5/2005 | Kenten et al. |
| 6,972,173 B2 | 12/2005 | Su et al. |
| 7,018,802 B2 | 3/2006 | Martin et al. |
| 7,022,287 B2 | 4/2006 | Schoeniger et al. |
| 7,160,735 B2 | 1/2007 | Dehlinger et al. |
| 7,176,036 B2 | 2/2007 | Wang et al. |
| 7,314,711 B2 | 1/2008 | Richter et al. |
| 7,517,701 B2 | 4/2009 | Parker et al. |
| 7,553,448 B2 | 6/2009 | Kumar et al. |
| 7,682,788 B2 | 3/2010 | Sigal et al. |
| 7,741,033 B2 | 6/2010 | Kelley et al. |
| 7,833,406 B2 | 11/2010 | Hori et al. |
| 8,044,390 B2 | 10/2011 | Hosokawa et al. |
| 8,106,391 B2 | 1/2012 | Endo et al. |
| 2003/0059839 A1 | 3/2003 | Obiso et al. |
| 2003/0118477 A1 | 6/2003 | Liljestrand et al. |
| 2003/0215845 A1 | 11/2003 | Bille |
| 2004/0058389 A1 | 3/2004 | Wang et al. |
| 2004/0067503 A1 | 4/2004 | Tan et al. |
| 2004/0096368 A1 | 5/2004 | Davis et al. |
| 2004/0129579 A1 | 7/2004 | Crooks et al. |
| 2004/0175742 A1 | 9/2004 | Hofmann et al. |
| 2004/0253624 A1 | 12/2004 | Smith et al. |
| 2005/0084881 A1 | 4/2005 | Kelley et al. |
| 2005/0136497 A1 | 6/2005 | Tsionsky et al. |
| 2005/0214565 A1 | 9/2005 | Ikeda et al. |
| 2006/0078912 A1 | 4/2006 | Bard et al. |
| 2006/0223084 A1 | 10/2006 | Carlson |
| 2007/0034529 A1 | 2/2007 | Bard et al. |
| 2008/0157403 A1 | 7/2008 | Lee et al. |
| 2009/0065371 A1 | 3/2009 | Ziao et al. |
| 2009/0270266 A1 | 10/2009 | Kelley et al. |
| 2010/0140086 A1 | 6/2010 | Sigal et al. |
| 2010/0187512 A1 | 7/2010 | Ito |
| 2010/0219404 A1 | 9/2010 | Endo et al. |
| 2010/0283043 A1 | 11/2010 | Nishimura et al. |
| 2010/0289013 A1 | 11/2010 | Ito et al. |
| 2010/0295029 A1 | 11/2010 | Kawamura |
| 2010/0295030 A1 | 11/2010 | Kawamura |
| 2010/0301312 A1 | 12/2010 | Jinde et al. |
| 2010/0301313 A1 | 12/2010 | Ito et al. |
| 2010/0320451 A1 | 12/2010 | Kawamura |
| 2010/0320452 A1 | 12/2010 | Kawamura |
| 2010/0327266 A1 | 12/2010 | Kawamura |
| 2011/0001130 A1 | 1/2011 | Nishimura et al. |
| 2011/0017983 A1 | 1/2011 | Mizuki et al. |
| 2012/0043225 A1 | 2/2012 | Zhou et al. |

FOREIGN PATENT DOCUMENTS

| | | |
|---|---|---|
| WO | WO 90/05302 A1 | 5/1990 |
| WO | WO 92/14139 | 8/1992 |
| WO | WO 96/21154 A1 | 7/1996 |
| WO | WO 96/35697 A1 | 11/1996 |
| WO | WO 03/089906 A2 | 10/2003 |
| WO | WO 2005/062982 | 7/2005 |
| WO | WO 2008/157403 | 12/2008 |
| WO | WO 2009/057430 | 5/2009 |
| WO | WO 2009/137002 A2 | 11/2009 |

OTHER PUBLICATIONS

Bertoncello, P. et al. "Nanostructured materials for electrochemiluminescence (ECL)-based detection methods: Recent advances and future perspectives," Biosensors and Bioelectronics 24 (2009) 3191-3200.*
Abstract of JP 06-300763, publication date Oct. 28, 1994, 1 page.
Abstract of JP 09-184841, publication date Jul. 15, 1997, 1 page.
Abstract of JP 09-184842, publication date Jul. 15, 1997, 2 pages.
Abstract of JP 2004-361334, publication date Dec. 24, 2004, 1 page.
An et al., Enhanced Emission and Its Switching in Fluorescent Organic Nanoparticles, J. Am. Chem. Soc., May 15, 2002, pp. 14410-14415., vol. 124, No. 48.
Bae et al., Electrochemistry and Electrogenerated Chemiluminescence of CdTe Nanoparticles, Nano Letters, 2004, pp. 1153-1161 vol. 4, No. 6.
Bard et al., Electrochemistry and Electrogenerated Chemiluminescence of Semiconductor Nanocrystals in Solutions and in Films, Struc Bond, Sep. 23, 2005, pp. 1-57, vol. 118.
Chang et al., Electrogenerated Chemiluminescence of Single Conjugated Polymer Nanoparticles, J. Am. Chem. Soc., May 9, 2008, pp. 8906-8907, vol. 130, No. 28.
Chen, Gold Nanoparticle-Modified ITO Electrode for Electrogenerated Chemiluminescence: Well-Preserved Transparency and Highly Enhanced Activity, Langmuir, 2007, pp. 11387-11390, vol. 23, No. 23.
Chovin et al., Development of an Ordered Microarray of Electrochemiluminescence Nanosensors, Measurement of Science and Technology, May 1, 2006, pp. 1211-1219, vol. 17, No. 5.
Cui et al., Multichannel Electrochemiluminescence of Luminol in Neutral and Alkaline Aqueous Solutions on a Gold Nanoparticle Self-Assembled Electrode, Analytical Chemistry, Jul. 15, 2004, pp. 4002-4010., vol. 76, No. 14.
Cui et al., Multichannel Electrogenerated Chemiluminescence of Lucigenin in Neutral and Alkaline Aqueous Solutions on a Gold

(56) References Cited

OTHER PUBLICATIONS

Nanoparticle Self-Assembled Gold Electrode, Journal of ElectroAnalytical Chemistry, Jul. 25, 2006, pp. 37-46, vol. 595.
Ding et al., Electrochmistry and Electrogenerated Chemiluminescence from Silicon Nanocrystal Quantum Dots, Science Magazine, May 17, 2002, pp. 1293-1297, vol. 296.
English abstract for JP 2006-061061 published Mar. 9, 2006.
English abstract for JP 2006-337351 published Dec. 14, 2006.
English abstract for JP 2006-343156 published Dec. 21, 2006.
English abstract for JP 2007-232676 published Sep. 13, 2007.
English abstract for WO 2006 038686 published Apr. 13, 2006.
Fan et al., An Electrochemical Coulomb Staircase: Detection of Single Electron-Transfer Events at Nanometer Electrodes, Science Magazine, Sep. 19, 1997, 3 pages, vol. 277.
Fan et al., Observing Single Nanoparticle Collisions by Electrogenerated Chemiluminescence Amplification, Nano Letters, May 21, 2008, pp. 1746-1749, vol. 8, No. 6.
Fraser et al., "Synthesis of Halomethyl and Other Bipyridine Derivatives by Reaction of 4,4'-Bis[(trimethylsilyl0methyl]-2,2'-bipyridine with Electophiles in the Presence of Fluoride Ion," *J* Orgn. Chem., 1997, vol. 62, pp. 9314-9317, 5 pages with cover sheet.
Fu et al., "Size Effects on the Optical Properties of Organic Nanoparticles," *J* Am Chem Soc, 2001, vol. 123, pp. 1434-1439.
Fu et al., Multiple Emissions for 1,3-Diphenyl-5-pyrenyl-2-pyrazoline Nanoparticles: Evolution from Molecular to Nanoscale to Bulk Materials, Angew. Chem. Int. Ed., 2002, pp. 962-965, vol. 41, No. 6.
Gill et al., "Pt Nanoparticles Functionalized with Nucleic Acid Act as Catalytic Labels for the Chemiluminescent Detection of DNA and Proteins," Small, 2006, vol. 2, pp. 1037-1041, 7 pages with cover sheets.
Grey et al., Size-Dependent Spectroscopic Properties of Conjugated Polymer Nanoparticles, J. Phy. Chem., Nov. 30, 2006, pp. 25568-25572, vol. 110, No. 51.
Guo et al., A New Electrogenerated Chemiluminescence Peak of Lucigenin in the Hydrogen-Evolution Region Induced by Platinum Nanoparticles, J. Phys. Chem. C, Dec. 2, 2006, pp. 606-611, vol. 111, No. 2.
He et al, Photostable Luminescent Nanoparticles as Biological Label for Cell Recognition of System Lupus Erythematosus Patients, Journal of Nanoscience and Nanotechnology, 2002, vol. 2, No. ¾, pp. 317-320.
Henglein et al., Absorption Spectrum and Some Chemical Reactions of Colloidal Platinum in Aqueous Solution, J. Phys. Chem., Jul. 12, 1995, pp. 14129-14136, vol. 99, No. 38.
International Search Report and Written Opinion for PCT/US2009/002160, mail date Jul. 31, 2009, 15 pages.
Japanese Publication JP2007232675, Gene Detection Method, dated Sep. 13, 2007, 14.
Kang et al., "Colloid Chemical Reaction Route to the Preparation of Nearly Monodispersed Perylene Nanoparticles: Size-Tunable Synthesis and Three-Dimensional Self-Organization," *J* Am Chem Soc, 2007, vol. 129, pp. 7305-7312.
Kasai et al., "Optical Properties of Perylene Microcystals," Mol. Cryst. Liq. Cryst., 1997, vol. 294, pp. 173-176.
Kasai et al., A Novel Preparation Method of Organic Microcrystals, Jpn. J. Appl. Phys., Aug. 1992, pp. L 1132-L 1134, Part 2, No. 8A.
Kasai et al., Crystal. Size Dependence of Emission from Perylene Microcrystals, Chemistry Letters, Jul. 11, 1997, pp. 1181-1182.
Kwon et al., "Surface structure effect on optical properties of organic nanocystals," Chemical Physics Letter, 2007, vol. 441, 5 pages.
Miao et al., Electrogenerated Chemiluminescence 69: The Tris (2,2'-bipyridine)ruthenium(II), $(Ru(bpy)_3^{2+})$//Tri-*n* -propylamine (TPrA) System Revisited-A New Route Involving TPrA$^{\cdot+}$Cation Radicals, JACS Articles, vol. 124, 2002, pp. 14478-14485.
Miao et al., Electrogenerated Chemiluminescence. 72. Determination of Immobilized DNA and C-Reactive Protein on Au(111) Electrodes Using Tris (2,2'-bipyridyl)ruthenium(II) Labels, Analytical Chemistry, Nov. 1, 2003, pp. 5825-5834, vol. 75, No. 21.
Miao et al., Electrogenerated Chemiluminescence. 77. DNA Hybridization Detection at High Amplification with $[Ru(bpy)_3]^{2+}$-Containing Microspheres, Analytical Chemistry, Sep. 15, 2004, pp. 5379-5386, vol. 76, No. 18.
Miao et al., Electrogenerated Chemiluminescence. 80. C-Reactive Protein Determination at High Amplification with $[Ru(bpy)_3]^{2+}$-Containing Microspheres, Analytical Chemistry, Dec. 1, 2004, pp. 7109-7113, vol. 76, No. 23.
Myung et al., Electrogenerated Chemiluminescence of CdSe Nanocrystals, Nano Letters, Oct. 22, 2002, pp. 1315-1319, vol. 2, No. 11.
Myung et al., Electrogenerated Chemiluminescence of GE Nanocrystals, Nano Letters, Dec. 5, 2003, pp. 183-185, vol. 4, No. 1.
Niazov et al., "Photoswitchable Electrocatalysis and Catalyzed Chemiluminescence Using Photoisomedzable Monolayer-Functionalized Surfaces and Pt Nanoparticles," *J* Am Chem Soc, 2007, vol. 129, pp. 6374-6375, 4 pages with cover sheets.
Omer et al., Electrogenerated Chemiluminescence of Aromatic Hydrocarbon Nanoparticles in an Aqueous Solution, J. Phys. Chem., Apr. 7, 2009, 4 pages, vol. xxx, No. xx.
Palacios et al., "Single Molecule Spectroelectrochemistry (SMS-EC)," *J* Am Chem Soc, 2006, vol. 128, pp. 9028-9029.
Palacios et al., Charging and Discharging of Single Conjugated-Polymer Nanoparticles, Nature Materials, Sep. 2007, pp. 680-685, vol. 6.
Palmer et al., 2,2'-Bipyridine Complexes, Inorganic Chemistry, vol. 5, No. 5, May 1966, pp. 864-878.
Polsky et al., "Nucleic Acid-Functionalized Pt Nanoparticles: Catalytic Labels for the Amplified Electrochemical Detection of Biomolecules," Anal. Chem., 2006, vol. 78, pp. 2268-2271, 6 pages with cover sheets.
Richter et al., Electrochemistry and electrogenerated chemiluminescence of films of the conjugated polymer 4-methoxy-(2-ethylhexoxyl)-2, 5-polyphenylenevinylene, Chemical Physics Letters, 1994, vol. 226, pp. 115-120.
Richter, Electrochemical Light, From Laboratory Curiosity to Useful Analytical Technique, Chem. Educator 2002, 7, 195-199.
Sonnichsen et al., "A Molecular Ruler Based on Plasmon Coupling of Single Gold and Silver Nanoparticles," Nature Biotechnology, 2005, vol. 23, pp. 741-745, 7 pages with cover sheets.
Szymanski et al., Single Molecule Nanoparticles of the Conjugated Polymer MEH-PPV, Preparation and Characaterization by Near-Field Scanning Optical Microscopy, J. Phys. Chem., Apr. 9, 2005, pp. 8543-8546, vol. 109, No. 18.
Tel-Vered et al., Generation and Detection of Single Metal Nanoparticles Using Scanning Electrochemical Microscopy Techniques, J. Phys. Chem, B, vol. 110, No. 50, 2006. pp. 25279-25287.
The Center for Electrochemistry, The University of Texas at Austin Newsletter, available at least by Nov. 6, 2008, 2 pages.
Wilson et al., Comparison Between Acridan Ester, Luminol, and Ruthenium Chelate Electrochemiluminescence, Electronoanalysis, 2001, pp. 1083-1092, vol. 13, No. 13.
Xiao et al., "Measurement of Single Molecule Conductance: Benzenedithiol and Benzenedimethanethiol," Nano Letters, 2004, vol. 4, pp. 267-271, 7 pages with cover sheets.
Xiao et al., "Observing Single Nanoparticle Collisions at an Ultramicroelectrode by Electrocatalytic Amplification," *J* Am Chem Soc, 2007, vol. 129, pp. 9610-9612.
Xiao et al., Current Transients in Single Nanoparticle Collision Events, J. Am. Chem. Soc., Nov. 19, 2008, pp. 16669-16677, vol. 130, No. 49.
Xiao et al., Observing Single Nanoparticle Collisions at an Ultramicroelectrode by Electrocatalytic Amplification, J. Am. Chem. Soc., Jul. 14, 2007, pp. 9610-9612, vol. 129, No. 31.
Yang et al., "Size effect in thiol and amine binding to small Pt nanoparticles," Analytica Chimica Acta, 2006, vol. 571, pp. 206-210.
Yu et al., Spontaneous Formation and Electrogenerated Chemiluminescence of Tri(bipyridine) Ru(II) Derivative Nanobelts, J. Am. Chem. Soc., Feb. 27, 2008, pp. 7196-7197, vol. 130, No. 23.
Zhang et al., "Single-Crystal 9, 10-diphenylanthracene Nanoribbons and Nanorods," Chem. Mater., 2008, vol. 20, pp. 6945-6950.

(56) References Cited

OTHER PUBLICATIONS

Zhang et al., Single-Crystal Nanoribbons, Nanotubes, and Nanowires from Intramolecular Charge-Transfer Organic Molecules, J. Am. Chem. Soc., Jun. 15, 2006, pp. 3527-3532, vol. 129, No. 12.

Zhou et al., "Scanning electrochemical microscopy Part 39. The proton:hydrogen mediator system and its application to the study of the electrocatalysis of hydrogen oxidation,"*J* Electroanal Chem, 2000, vol. 491, 11 pages.

Zu et al. Electrogenerated Chemiluminescence. 66. The Role of Direct Coreactant Oxidation in the Ruthenium Tris(2,2')bipyridyl/ Tripropylamine System and the Effect of Halide Ions on the Emission Intensity, Analytical Chemistry, Jul. 15, 2000, pp. 3223-3232, vol. 72, No. 14.

\* cited by examiner

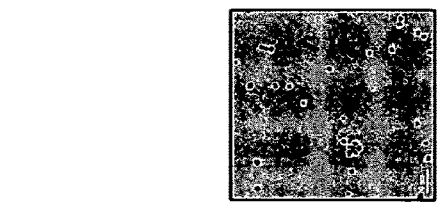
FIG. 5E
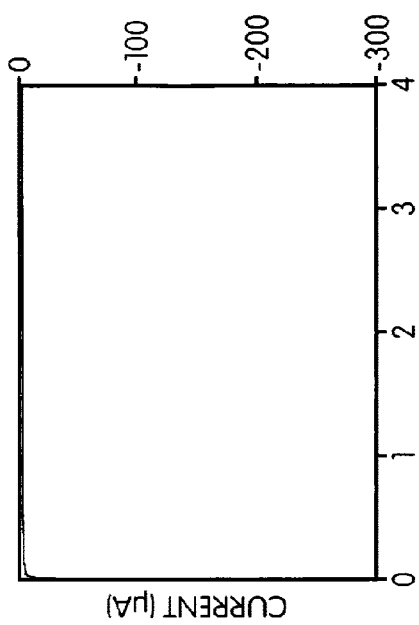
FIG. 5C
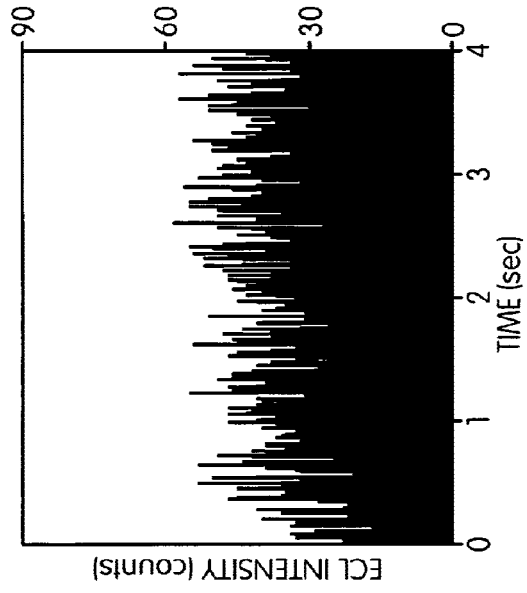
FIG. 5D
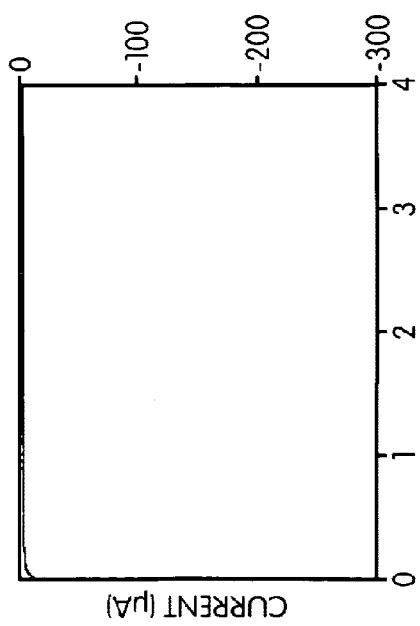
FIG. 5A
FIG. 5B

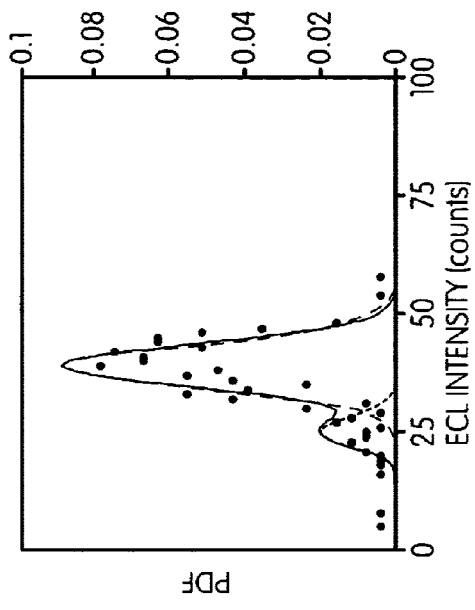
FIG. 9A
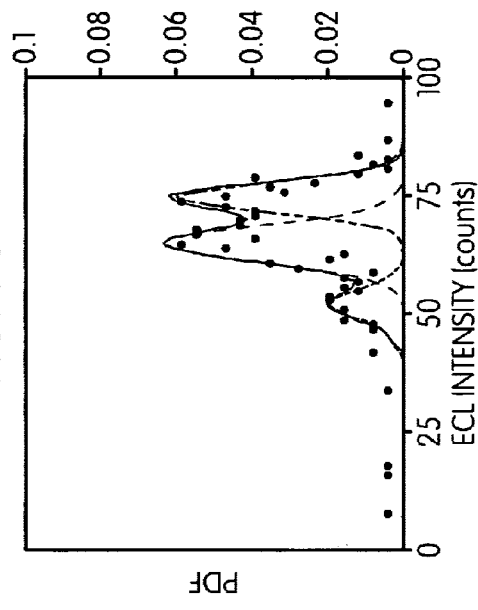
FIG. 9C
FIG. 9B
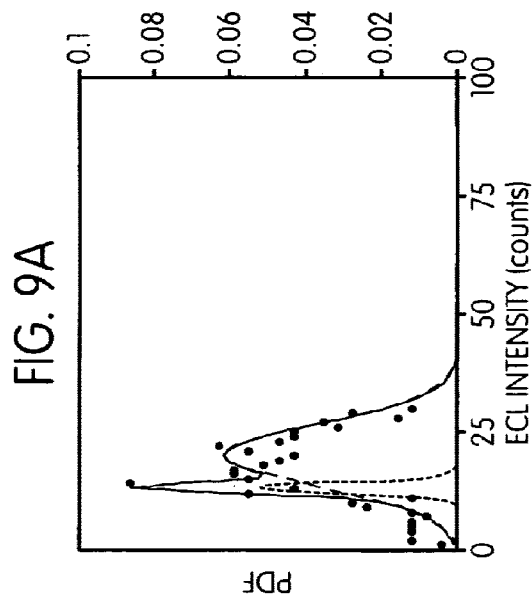
FIG. 9D

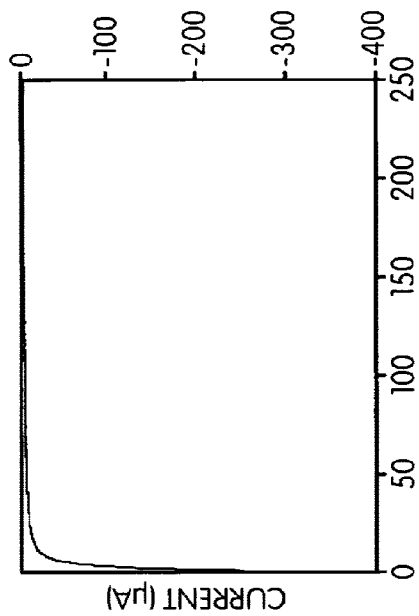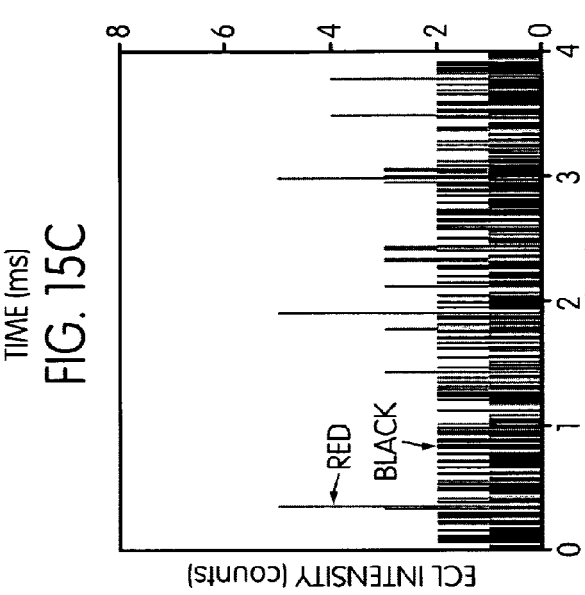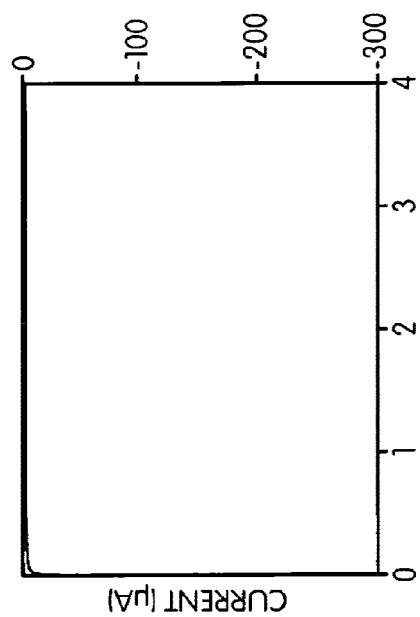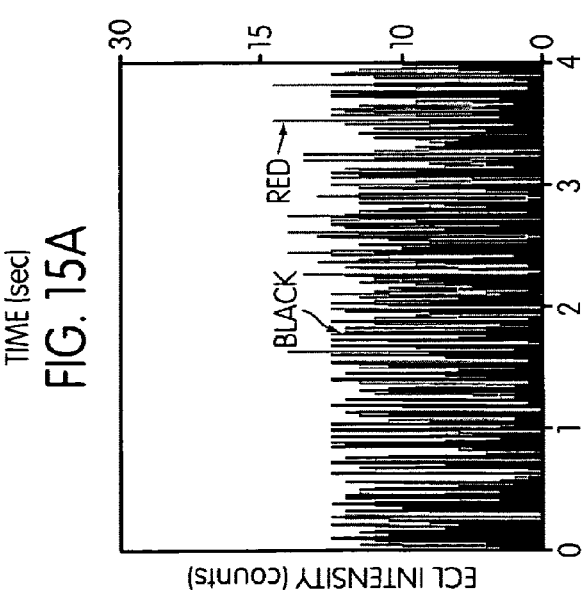
FIG. 15A
FIG. 15B
FIG. 15C
FIG. 15D

METHOD FOR NANOPARTICLE ELECTROGENERATED CHEMILUMINESCENCE AMPLIFICATION

CROSS-REFERENCE TO RELATED APPLICATIONS

This application is a divisional of U.S. patent application Ser. No. 12/936,675, which is a U.S. national stage of International Application No. PCT/US2009/002160, filed on Apr. 7, 2009, which claims the benefit of U.S. Provisional Patent Application 61/123,780, filed on Apr. 11, 2008; U.S. Provisional Patent Application 61/123,943, filed on Apr. 11, 2008; and U.S. Provisional Patent Application 61/124,935, filed on Apr. 21, 2008; the entire contents of which are hereby incorporated by reference, for any and all purposes.

BACKGROUND

The physical properties of nanoparticles ("NPs"), e.g., high surface-to-volume ratio, elevated surface energy, increased ductility after pressure loading, higher hardness, larger specific heat, and the like, have led to increased applications in the material-directed industry and material science. For example, a variety of metal NPs have been used to catalyze numerous reactions.

The size of NPs range from less than 1 nm to about 100 nm and the electronic energy band configuration is a size-dependent property, which in turn can affect the physical and chemical properties. A fundamental distinction between NPs and bulk materials is that the fraction of surface atoms and the radius of curvature of the surface of NPs is comparable with the lattice constant. As a result, nanostructured catalysts generally have a higher catalytic activity as compared with their analogues based on bulk materials. A number of methods of forming NPs are known to the skilled artisan and include formation by combining atoms (or more complex radicals and molecules) and by dispersion of bulk materials, e.g., thermal evaporation, ion sputtering, reduction from solution, reduction in microemulsions, and condensation.

Colloidal particles used in sensing arrays have been reported. These are chemical sensors for detecting analytes in fluids via arrays having a plurality of alternating nonconductive regions and conductive regions of conductive NP materials. Variability in chemical sensitivity from sensor to sensor is reported to be provided by qualitatively or quantitatively varying the composition of the conductive and/or nonconductive regions.

Single particle electrochemical sensors, which employ an electrochemical device for detecting single particles, have also been reported. Methods for using such a device to achieve high sensitivity for detecting particles such as bacteria, viruses, aggregates, immuno-complexes, molecules, or ionic species have also been described.

SUMMARY

The present application relates in general to the field of nanoparticles ("NPs"), and in particular, relates to instruments, methods and reagents for amplifying an electrogenerated chemiluminescence ("ECL") signal from a catalytic reaction using NPs. The difficulties in generating, locating, and characterizing a single NP, especially at the nm scale and in measuring the very small current and ECL intensity generated by these electrode reactions to NPs have been recognized. The present technology can potentially be applied to determine particle size distributions, surface film porosity, and as a very sensitive electroanalytical technique.

Adsorption of other species in the matrix on the electrode surface can interfere by passivating the electrode, as can nonspecific adsorption. The problem may typically be overcome by using clean electrochemical systems (cell and electrolyte), sample pretreatment, and/or by modifying the supporting electrode surfaces.

The present method and apparatus may be employed to detect a single nanoparticle collision event with an electrode through electrogenerated chemiluminescence ("ECL") reaction schemes. The single particle collision event produces a burst of light that can have highly sensitive analytical implications. This typically occurs by bringing a liquid sample, which includes a plurality of conductive or redox active nanoparticles and a plurality of electrogenerated chemiluminescent ("ECL") moieties, into contact with one or more electrodes in a sample chamber. Through these reactions, large amplification factors in the ECL intensity associated with those events can be achieved. For example, the oxidation of tri-n-propyl amine ("TPrA") in the presence of $Ru(bpy)_3^{2+}$ occurs rapidly at a platinum nanoparticle surface, but at a much slower rate at an indium tin oxide ("ITO") electrode surface within a certain potential window. As a result, every collision of a particle at the electrode surface produces a unique ECL-time profile which correlates with the particle size, the particle residence time, and the nature of the particle interaction with the electrode surface. This technology can be used to determine nanoparticle size distributions, to examine electron transfer kinetics, and especially as a very sensitive electroanalytical technique. It should have applications in nanotechnology, biotechnology and clinical analysis as a simple, low-cost, rapid, and ultra high-sensitivity analytical method by exploring and detecting single binding events between biomolecules (DNA hybridization, interactions between protein-DNA, antibody-antigen, protein-small molecules). Single molecule detection levels should be possible.

The present application provides a method and apparatus, which may be used for observing the ECL generated during collisions of single NPs at an electrode. The method and apparatus can provide information of electrochemical processes at single NPs, as well as the basis of highly sensitive electroanalytical methods. NPs have been shown to have a wide range of application in electronics, optics, catalysis, and biotechnology.

In one embodiment, the present application provides a method and device for analyzing a sample within a sample chamber. In this embodiment, the present method typically may include adding one or more conductive or redox active NPs to a liquid sample within a sample chamber, and observing current and/or ECL generated by the interaction of the conductive or redox active NPs and the liquid sample using one or more electrode. Typically, the observed electroanalytical property is an amplification of ECL intensity of an electrode reaction catalyzed by the conductive or redox active NPs. The observed property, however, is not limited to a current and may include other parameters, such as an ECL emission, other electrical parameters, or any combinations thereof.

The device disclosed in the present application commonly includes an electrochemical cell connected to a measuring apparatus which includes an electrochemical apparatus and a photon detector. The electrochemical cell (see, e.g., exemplary device depicted in FIG. 16) typically has one or more electrodes in a sample chamber and an electrochemical apparatus in communication with the electrodes. One or more conductive or redox active NPs may be injected into a sample in the sample chamber. The injected NPs can interact with the sample and generate one or more photons that can be observed with a photon detector. The device may optionally contain an indicator in a solution. In addition, the electrochemical cell may have a dimension in the nanometer scale and include ultramicroelectrodes ("UMEs").

The present application includes a kit for analyzing one or more chemical analyte(s) having at least one NP, at lease one chemical indicators, at least one electrode, and a measuring apparatus that reads one or more current and ECL properties generated by the interactions between the NP(s), the electrodes(s) and the chemical analytes(s).

In contrast to other amplification technologies, such as optical and electrical enhancement, the present ECL amplification scheme based on nanoparticles is particularly advantageous. The large amplification factors involved can allow one to observe single particle collision event. By studying an individual collision event, the multiple processes involved in such a single event can be further explored and analyzed, such as frequency-related particle concentration, amplitude-related particle size and the nature of particle binding to the electrode surfaces, and the like. Catalytic amplification using a monolayer of nanoparticles has already been widely demonstrated in biosensors and biotechnology. For the first time, the ECL amplification at a single nanoparticle has been demonstrated. Current methods used to study the single electron transfer event at a single particle, such as SEM and/or TEM, are expensive and slow techniques. Despite this, such techniques have been widely used to study particle size distributions. Light scattering is also used for this application. The present technique has the potential to determine the size distribution and in many cases the chemical identity of the nanoparticles. Fluorescence microscopy, surface plasmon resonance and enhanced Raman and vibrational spectroscopy are very useful in biotechnology to detect and screen the binding between biomolecules. The ECL technique can detect such interactions at the single molecule and single electron transfer event level with much less expensive and simpler apparatus. The present method has the advantage that a light source is not used, so that scattered light and interference from emission of luminescent impurities are not problems. It is also often more convenient than other chemiluminescent methods, since the electrochemical excitation can permit temporal and spatial control.

In many embodiments, the nanoparticles ("NPs") have a least one dimension which is no larger than about 200 nm, more commonly no more than about 100 nm and, in some embodiments, at least one dimension is no larger than about 50 nm. For example, the nanostructured material may be a nanoparticle ("NP") in which no dimension is larger than about 100 nm and, some instances, no larger than 20 nm. Other examples include nanocrystals ("NCs") in which typically at least two and, often three, dimensions are no more than about 200 nm and often no more than about 50 nm. Other embodiments may include nanobelts ("NBs"), which have long, straight and belt-like morphology, with a thickness of more than about 200 nm. Such nanobelts may have widths of about 200 to 1000 nm and lengths of up to about 5 to 15 μm and typically have a width-to-thickness ratio of about 5 to 10.

BRIEF DESCRIPTION OF THE DRAWINGS

For a more complete understanding of the features and advantages of the present method and apparatus, reference is now made to the detailed description section along with the accompanying figures and in which:

FIG. 5 is a graph of individual current transients (5A and 5C) and (ECL intensity vs. times) records (5B and 5D) at the ITO electrode before (5A and 5B) and after (5C and 5D) the injection of 2 nM Pt colloidal solution. The ITO potential is stepped from 0 to 0.91 V vs. SCE for a duration of 4 seconds. FIG. 5B total photon counts=8428. FIG. 5D total photon counts=9968. FIG. 5E shows a TEM image of representative platinum NPs, which have an average diameter of ~4 nm.

FIG. 8 shows graphs of different (ECL intensity vs. times) records resulting from different concentrations of the indicator species (concentration of Ru(bpy)$_3$$^{2+}$: 1.2 nM (8A), 2 nM (8B), 4 nM (8C) and 6 nM (8D)) but nearly the same concentrations of Pt NPs (concentration of Pt NPs: ~1.6 nM (8A, 8B, 8C) and ~2 nM (8D)) and coreactant at the ITO electrode. Es=0.91 V for FIGS. 8A-8D.

FIG. 9 illustrates the PDFs and their decomposed multinormal distributions, FIGS. 9A, 9B, 9C, and 9D, corresponding to the (ECL intensity vs. time) curves shown in FIGS. 8A, 8B, 8C, and 8D, respectively.

V. FIG. 11B (ECL+dark) counts=5216; Es=0.81 V. FIG. 11C (ECL+dark) counts=5821; Es=1.11 V.

FIG. 12 are PDFs of the ECL transients at the ITO electrode resulting from two different concentrations of the indicator species, $Ru(bpy)_3^{2+}$, (3 μM (12A) and 6 μM (12B)) in the absence of Pt NPs.

FIG. 13B total photon counts=9968.

FIG. 15 shows two parts of current transients (15A and 15C) and (ECL intensity vs. time) records (15B and 15D) at an ITO electrode in a solution before ("BLACK" curves) and after ("RED" curves) injection of ~2 nM Pt NPs. The solution contains 0.1 M $NaClO_4$, phosphate buffer (pH 7.0), 1.3 μM $Ru(bpy)_3(ClO_4)_2$ and 5 mM TPrA. The ITO potential is stepped from 0 to 0.91 V vs. SCE for two different time durations: 4 s (channel dwell time, $\tau_{ch}$=15.6 ms) in FIGS. 15A and 15B, and 250 ms ($\tau_{ch}$=75 μs) in FIGS. 15C and 15D.

DETAILED DESCRIPTION

Figure 1:
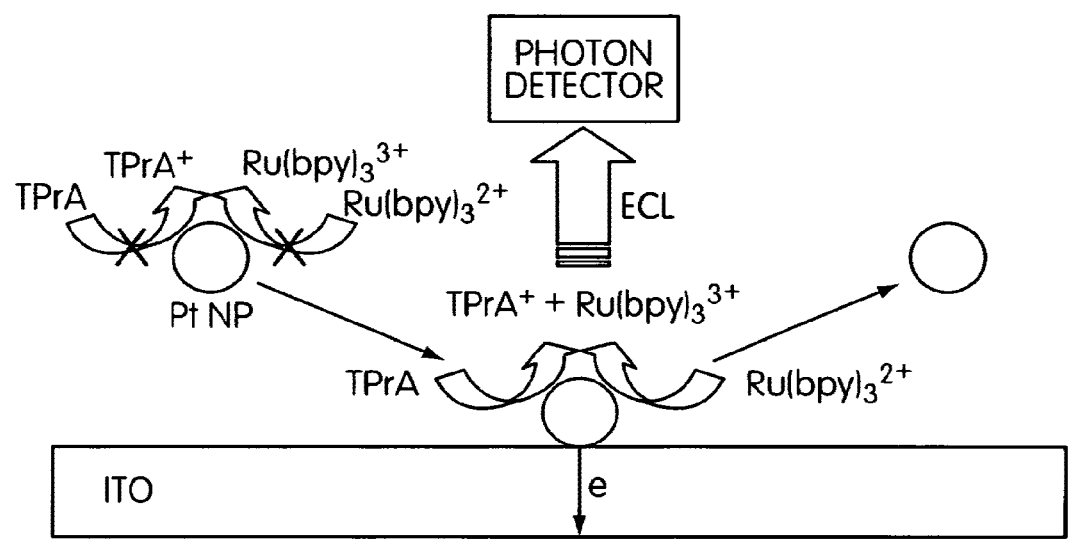
FIG. 1 is a schematic of the Pt NP collision/ECL generation event.

While making and using of various embodiments of the present method and apparatus are discussed in detail below, it should be appreciated that the present application provides many applicable inventive concepts that can be embodied in a wide variety of specific contexts. The specific embodiments discussed herein are merely illustrative of specific ways to make and use the present method and apparatus and are not intended to limit the scope of the invention.

The present application provides method based on the significant ECL intensity amplification factor involved in a rapid reaction of a species in single particle collision events. The reaction of the species in solution at the surface of the nanoparticle NP desirably does not produce significant ECL at the working electrode surface in the same potential region. In such situations, when the electrochemical cell is operated in such a potential region, significant ECL will only be generated from electrochemical generated events occurring at the surface of nanoparticles, which are in electrical contact with the working electrode (and not the working electrode itself).

The ECL moieties employed in the present methods are compounds, which are capable of being involved in a redox reaction resulting in electrogenerated species and the emission of light ("electrochemiluminescence"). For example, electrochemiluminescence may involve luminescence generated by a process in which one or more reactants are stimulated electrochemically and undergo one or more chemical reactions to produce species (derived from the ECL moieties) that emits light, preferably repeatedly. In other words, the ECL moieties are compounds which are capable of being converted via an electrochemically initiated redox reaction into a species which will emit light, generally at a wavelength in the visible spectrum. The ECL moieties may include a metal-containing complex. Suitable metals which may be included in such compounds include ruthenium, osmium, rhenium, cerium, europium, terbium, and/or ytterbium. Ruthenium-containing compounds with organic ligands are commonly employed in the present method. The metal-containing compound often include polydentate ligands, e.g., aromatic polydentate ligands such as bipyridyl, substituted bipyridyl, 1,10-phenanthroline and/or substituted 1,10-phenanthroline. Specific examples of suitable ECL moieties include compounds which include a bis(2,2'-bipyridyl)ruthenium(II) or tris(2,2'-bipyridyl)ruthenium(II) moiety. One group of such compound which can act as an ECL label are $Ru(bpy)_3^{2+}$ salts, e.g., $Ru(bpy)_3 Cl_2$.

The nanoparticles employed in the methods described herein can be produced by a variety of methods known to those of skill in the art. This include methods of forming NPs by combining atoms (or more complex radicals and molecules) and by dispersion of bulk materials, e.g., thermal evaporation, ion sputtering, reduction from solution, reduction in microemulsions and condensation. For example, platinum NPs may be produced from a solution prepared by combining aqueous $H_2PtCl_6$ solution with aqueous sodium citrate solution and then, under vigorous stirring, adding aqueous $NaBH_4$ solution dropwise. The solution was kept stirring for another half hour. The skilled artisan will recognize that other solutions containing colloidal nanoparticles may similarly be prepared, e.g., colloidal solutions of platinum, palladium or ruthenium nanoparticles.

The size of NPs produced by such methods can range from less than 1 nm to about 100 nm. More commonly, a range for the average size of such nanoparticles is about 1 nm to 10 nm in diameter and may be about 2 to 7 nm in diameter. Suitable nanoparticles, e.g., conductive platinum nanoparticles, can have a size range of about 2 nm to 6 nm in diameter with an average diameter of about 4 nm.

The solutions of colloidal NPs employed in the present methods may have a concentration of the colloidal NPs in the pM to nM range. In many instances, NP concentrations of about 1 to 10 nM are employed. Such solutions can be conveniently prepared by adding aliquots, e.g., 10 to 100 μL aliquots of a stock solution containing about 0.1 μM (100 nM) colloidal NPs, to a larger volume (e.g., circa 5 mL) of a sample solution. For some applications, sample solutions containing about 100 pM colloidal nanoparticles or less may be employed.

In the present methods, the sample solutions typically contain much higher concentrations of the ECL label compound and optional coreactant. For example, when the concentration of the colloidal NPs is in the pM to nM range, the present methods may suitably be conducted with sample solutions which include about 1 to 20 μM of an ECL label compound, e.g., an $Ru(bpy)_3^{2+}$ salt, and about 1 to 100 mM of a ECL coreactant, such as TPrA.

FIG. 1 is a schematic of a single platinum NP collision event. The particle diffuses to the electrode where it collides and catalyses some oxidation reactions (in this schematic $Ru(bpy)_3^{2+}$ and TPrA) during the residence time. The collisions of single platinum NPs at an electrode were observed electrochemically by their characteristic (ECL intensity vs. time) transients for particle-catalyzed reactions. A single event is characterized by the ECL generated by electrocatalyzed reactions of an indicator species and a coreactant (e.g., $Ru(bpy)_3^{2+}$ and TPrA) present in the solution. Since electrocatalyzed reactions do not occur at the selected electrode at the potential of interest and can involve a high concentration of indicator species and coreactant with much larger diffusion coefficients than the NP, significant amplification in the ECL intensity occurs. Every collision produces a unique (ECL intensity vs. time) profile that can be correlated with the particle size, the particle residence time and the nature of the NP interaction with the electrode surface. The present method also allows the study of heterogeneous kinetics at single NPs and the application of a very sensitive electroanalytical technique.

At a planar macroelectrode, e.g. an indium tin oxide ("ITO") electrode immersed in a dispersion of 2 nM Pt NPs in 0.1 M $NaClO_4$ solution containing phosphate buffer (pH ~7.5), 10 μM $(Ru(bpy)_3^{2+}$ and 50 mM tri-n-propyl amine ("TPrA") as a coreactant, the diffusion-controlled flux of particles to the electrode surface, $J_{p,s}$, when the particles adhere to the surface, is given by:

$$J_{p,s} = D_p^{1/2} C_p / \pi^{1/2} t^{1/2}$$

where $D_p$ is the particle diffusion coefficient and $C_p$ is the particle concentration. Ordinarily, in the simple NP or nanoelectrode faradaic or charging process, only one or a few electrons ($n_p$) would transfer between the NP and the electrode to yield a current, $i_{p,s} = n_p F A_e J_{p,s}$ (where $A_e$ is the electrode area and F is the Faraday constant), that is much too small to observe above the background current level. However, on an ultramicroelectrode ("UME") of radius $r_0$, the current for a collision is a transient that includes particle charging and a changing faradaic current for R oxidation that attains steady state in the time $\sim r_O^2 / D_R$, in which $D_R$ is the diffusion coefficient of R. Since different types of collision can occur, the current-time ("i-t") transient for each collision event will be determined by the residence time, T, of the particle at the electrode, i.e., the time period when the electrode can pass electrons to the particle. If the particle sticks to the electrode for a time sufficient for a steady state current to be attained, and the reactant R of concentration $C_R$ is only oxidized at the particle of radius a, an amplification factor given by the relative steady-state fluxes of the particles and R, is $\sim (B/16)(D_R C_R a)/(D_p C_p r_O)$. This will lead to relative steady-state currents of $\sim B(D_R C_R r_O)/4(D_p C_p a)$ (assuming $n_p = n_R$, $n_R$ is the number of electrons involved in the reaction). For a 1 pM particle solution and 10 mM indicator R, the estimated amplification factor for a 1 nm radius particle can be nine to ten orders of magnitude, assuming the diffusion coefficient of the particle are different by about an order of magnitude. Methods and reagents for amplifying current from a catalytic reaction using metal NPs are herein described and provided.

Figure 2A:
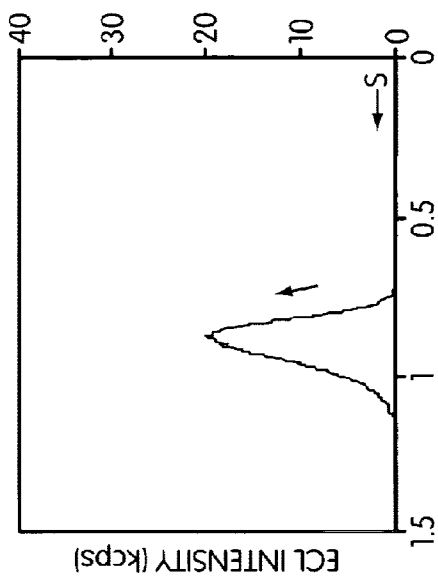
FIG. 2 shows cyclic voltammograms (2A and 2C) and (ECL intensity vs. potential) curves (2B and 2D) in a solution containing Ru(bpy)$_3$$^{2+}$ and tri-n-propyl amine ("TPrA") at a macro Pt (2A and 2B) or ITO (2C and 2D) electrode.
Figure 2B:
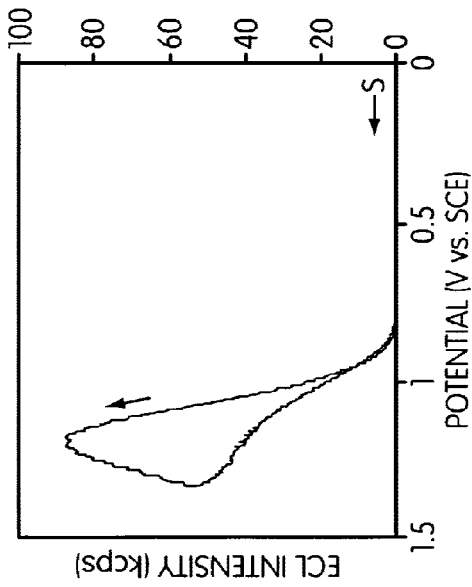
Figure 2C:
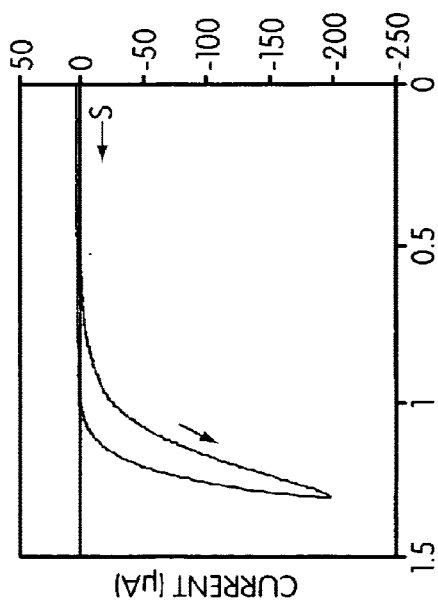
Figure 2D:
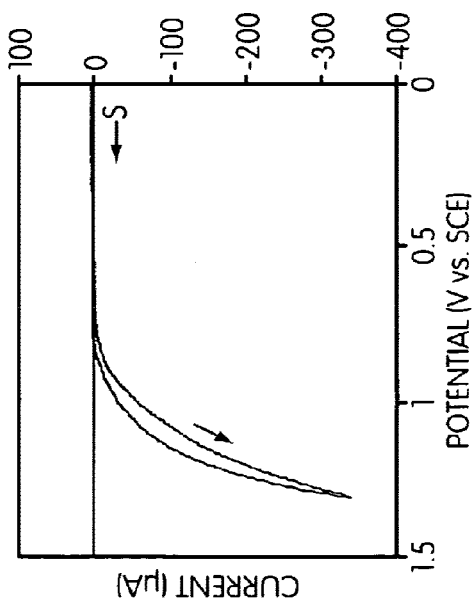

As shown in FIG. 2D, the reactions of the indicator species and the coreactant at relatively high concentration in the solution do not generate an appreciable ECL intensity at an ITO electrode at potentials negative of 0.88 V while significant ECL intensity can easily be observed at a Pt disk electrode at a potential of 0.75 V vs. SCE (see FIG. 2B) at the same solution conditions. The corresponding cyclic voltammograms are shown in FIGS. 2A and 2C.

Figure 3A:
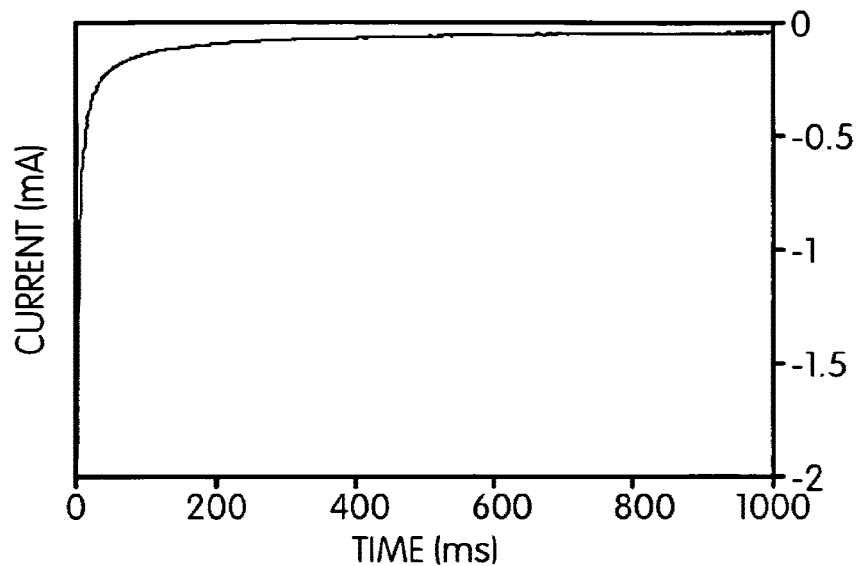
FIG. 3 shows current transient (3A) and (ECL intensity vs. time) curve (3B) at a macro Pt disk electrode.
Figure 3B:
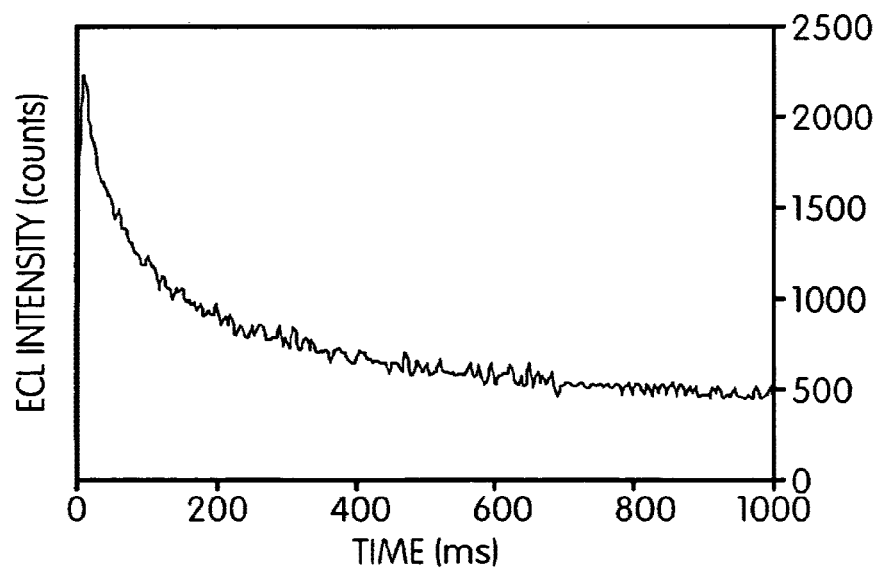

FIG. 3 are current transient (3A) and (ECL intensity vs. times) curve (3B) at a macro Pt disk electrode in 0.1 M $NaClO_4$ solution containing 25 mM phosphate buffer (pH ~7.5), saturated $(Ru(bpy)_3(ClO_4)_2$ and 50 mM TPrA. Both current and ECL transients were smooth curves with small noise levels.

Figure 4A:
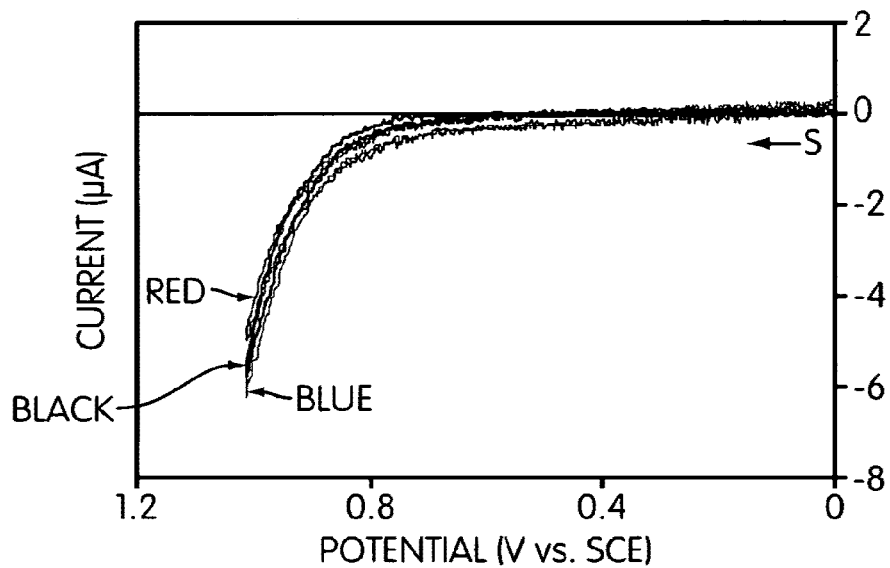
FIG. 4 shows cyclic voltammograms ("CVs"; 4A) and (ECL intensity (kilocounts per sec, "kcps") vs. potential) curves (4B) at an ITO electrode in solutions containing different concentrations of Pt NPs: 0 nM Pt NPs "BLACK"; ~1 nM Pt NPs "RED"; and ~2 nM Pt NPs "BLUE".
Figure 4B:
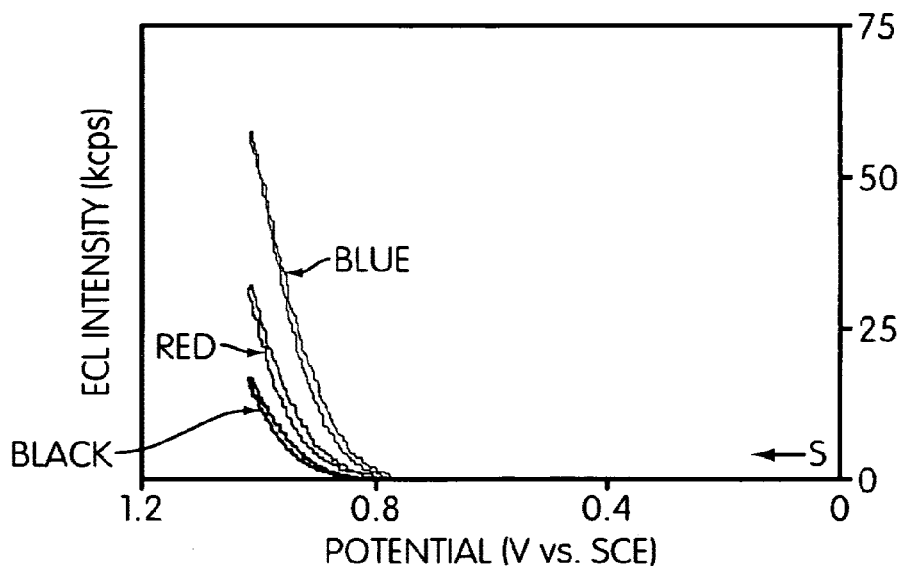

FIG. 4 shows cyclic voltammograms (4A) and ECL intensity (kilocounts per sec, "kcps") vs. potential curves (4B) at an ITO electrode in a solution before injecting PT NPs ("BLACK" curves), after injecting ~1 nM Pt NPs ("RED" curves), and after injecting ~2 nM Pt NPs ("BLUE" curves). The solutions contain 0.1 M $NaClO_4$, phosphate buffer (pH 7.0), 10 μM $Ru(bpy)_3(ClO_4)_2$ and 50 mM TPrA. Potential scan rate=20 mV/from point s. On an ITO, in the absence of Pt NPs, as shown in the "BLACK" curve of FIG. 4B, no appreciable ECL intensity was observed until its potential was slightly positive of 0.85 V vs. SCE, while significant current started to flow at potentials near ~0.6 V (see the "BLACK" curve of FIG. 4A). However, if the NP is present and can electrocatalyze other reactions, say oxidation of a species R to O (e.g., oxidation of $(Ru(bpy)_3^{2+}$ or TPrA) at a Pt NP upon its contact with the ITO, a significant enhancement in the ECL intensity as shown in the "RED" curve of FIG. 4B can be observed at lower bias potential (≤0.75 V). Notice that the enhancement in ECL intensity, as shown in FIG. 4B, increases with increasing concentrations of Pt NPs, indicating that the ECL enhancement is associated with the Pt NPs induced electrochemical reaction upon their contact with the ITO.

In one embodiment of the present method, FIG. 5 shows the current transients at an ITO electrode in a solution before and after injecting platinum particles. FIG. 5A is a graph of the current transients at an ITO electrode in 3 μM $Ru(bpy)_3^{2+}$ and 5 mM TPrA in the absence of platinum NPs; FIG. 5C is a graph of the current transients at an ITO electrode in 3 μM $Ru(bpy)_3^{2+}$ and 5 mM TPrA in the presence of ~2 nM Pt NPs. FIG. 5B (total photon counts=8428) is the corresponding (ECL intensity vs. time) curve for FIG. 5A. FIG. 5D (total photon counts=9968) is the corresponding (ECL intensity vs. time) curve for FIG. 5C. FIG. 5E is a TEM image of representative platinum NPs, which have an average diameter ~4 nm. The ITO potential was stepped from 0 to 0.91 V vs. SCE for a duration of 4 seconds.

The platinum colloidal solution was obtained by reducing $H_2PtCl_6$ with sodium borohydride in the presence of sodium citrate. The particle sizes were between about 2 to 6 nm, with a major distribution at 4 nm in diameter. In some embodiments, about 40 μL Pt colloidal solutions (~0.1 μM Pt NPs) were injected into 4 mL buffered electrolyte solution to get ~1 nM Pt NPs in the electrochemical cell. After mixing the solution well, the current transient and the (ECL intensity vs. time) response were recorded by applying a step potential of desired amplitude on the supporting electrode and monitoring simultaneously the variation in the current and ECL intensity with time.

Figure 6C:
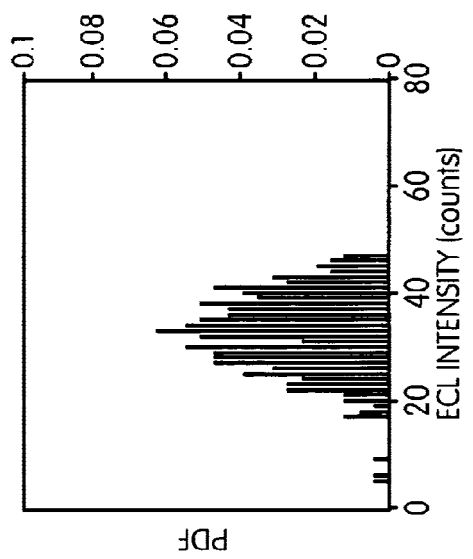
FIG. 6 shows ECL transients (6A and 6B) and the corresponding probability density functions ("PDFs") (6C and 6D) of ECL transients at the ITO electrode before (6A and 6C) and after (6B and 6D) the injection of ~2 nM Pt NP solution. The ITO potential is stepped from 0 to 0.91 V vs. SCE for a duration of 4 seconds.
FIG. 6A total photon counts=8428.
FIG. 6B total photon counts=9968.
Figure 6D:
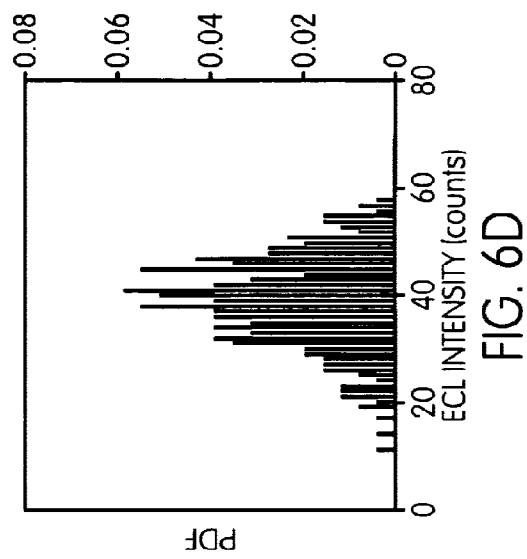
Figure 6A:
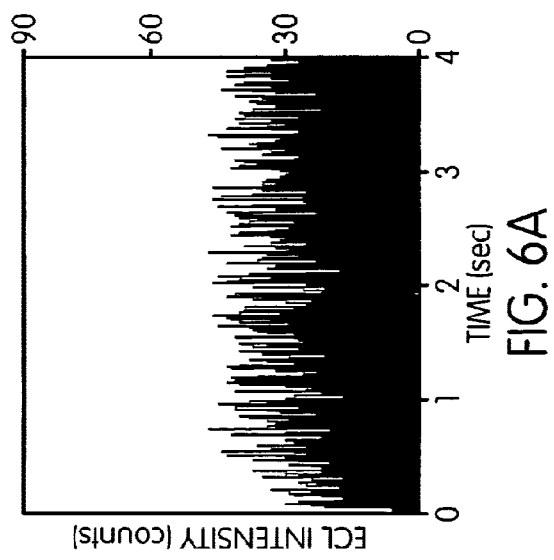
Figure 6B:
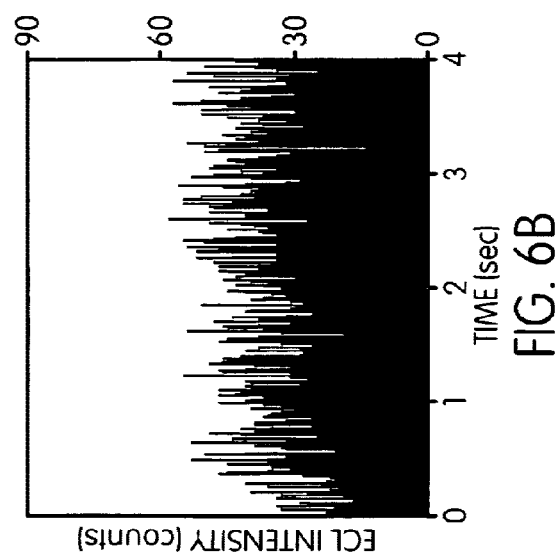
Figure 7A:
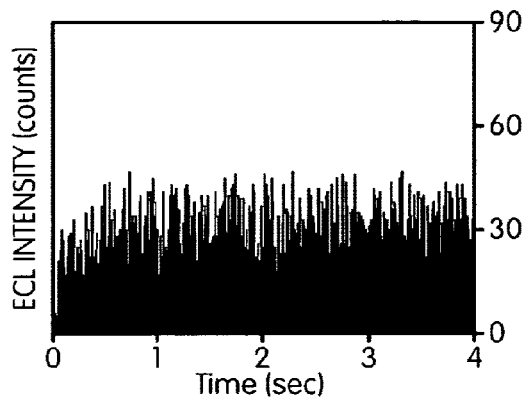
FIG. 7A total photon counts=8428.
Figure 7D:
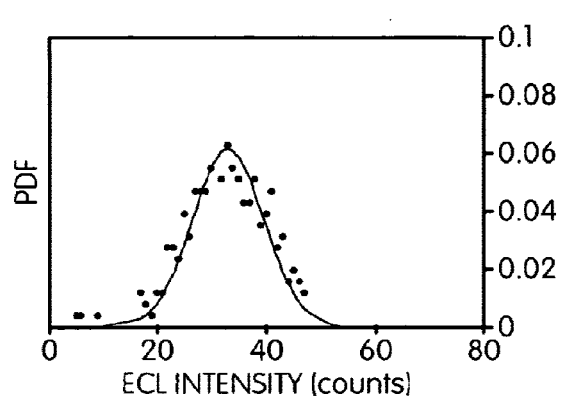
FIG. 7 shows the (ECL intensity vs. times) curves (7A, 7B and 7C) and the corresponding PDFs (7D, 7E, and 7F respectively) and their decomposed Gaussian distributions at the ITO electrode at three difference colloidal Pt NP concentrations (0 nM Pt NPs (7A and 7D); ~1 nM Pt NPs (7B and 7E); and ~2 nM Pt NPs (7C and 7F)) but at nearly the same concentrations of the indicator species and coreactant. The ITO potential is stepped from 0 to 0.91 V vs. SCE for a duration of 4 seconds.
FIG. 7B total photon counts=9247.
FIG. 7C total photon counts=9968.
Figure 7B:
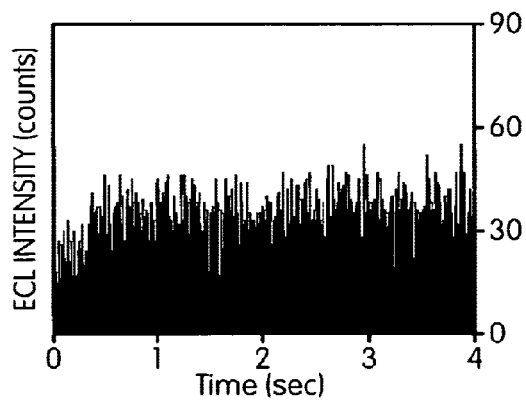
Figure 7E:
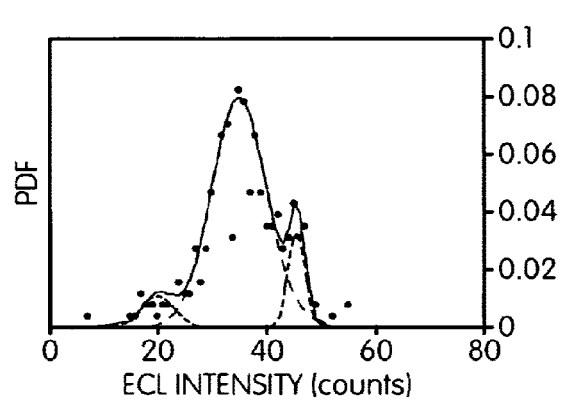
Figure 7C:
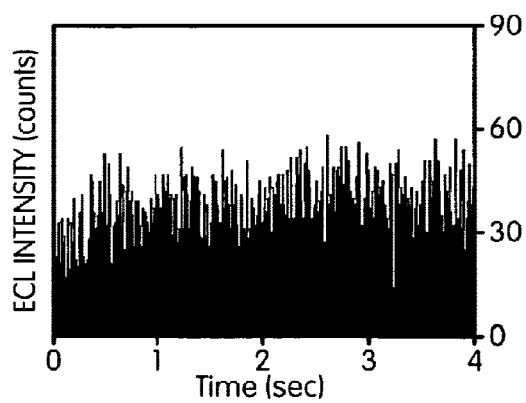
Figure 7F:
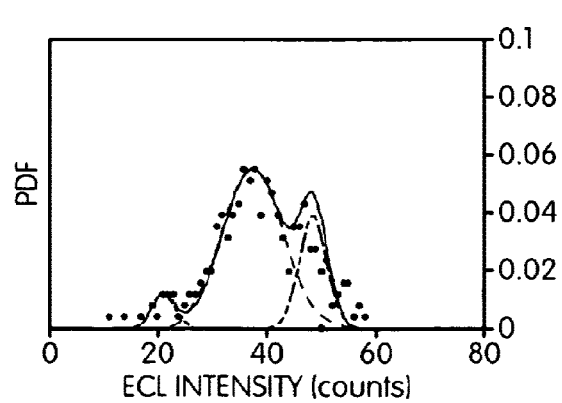
Figure 8A:
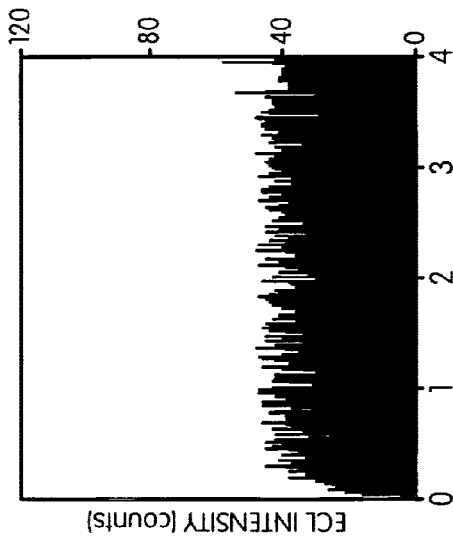
FIG. 8A total photon counts=1913.
Figure 8B:
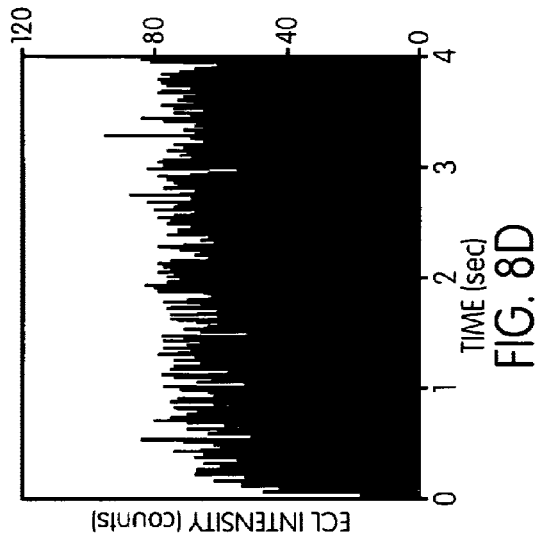
FIG. 8B total photon counts=4538.
Figure 8C:
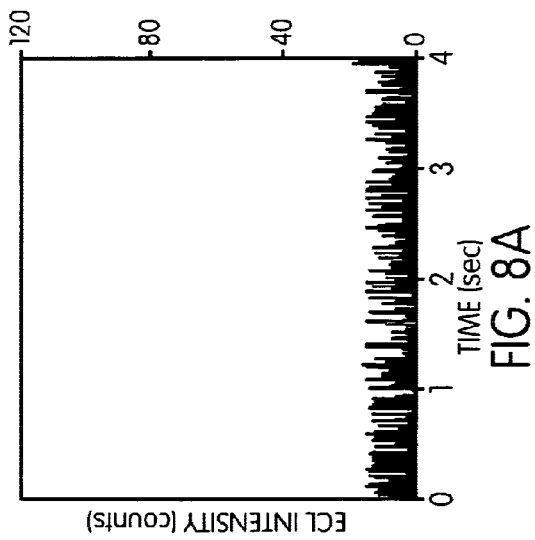
FIG. 8C total photon counts=9781.
Figure 8D:
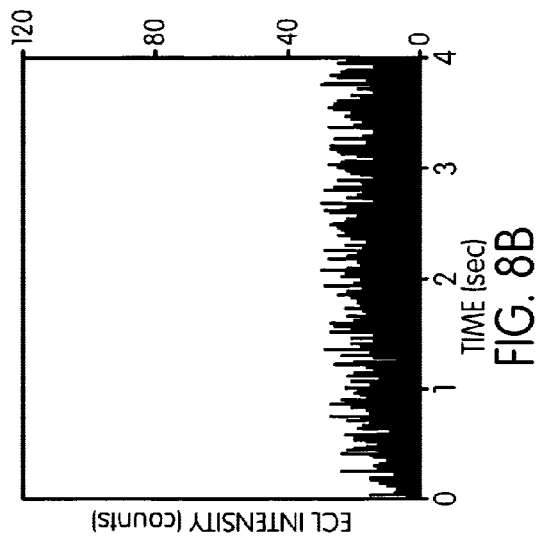
FIG. 8D total photon counts=17166.
Figure 10A:
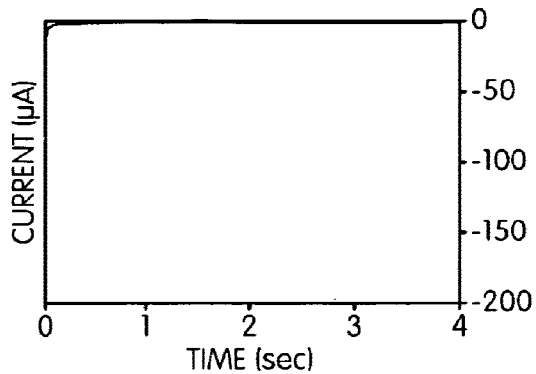
FIG. 10 is a graph that illustrates the current transients (10A, 10B, 10C) and the corresponding (ECL intensity vs. time) records (10D, 10E, 10F) at the ITO electrode with ~1 nM Pt NPs at different applied step potentials: 0.71 V vs. SCE (10A, 10D), 0.81 V vs. SCE (10B, 10E) and 1.11 V vs. SCE (10C, 10F).
FIG. 10D (ECL+dark) counts=2222.
FIG. 10E (ECL+dark) counts=5216.
FIG. 10F (ECL+dark) counts=5821.
Figure 10D:
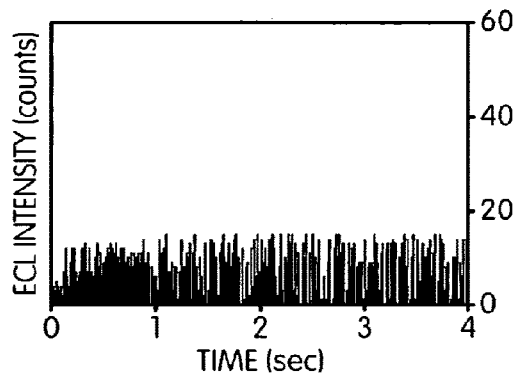
Figure 10B:
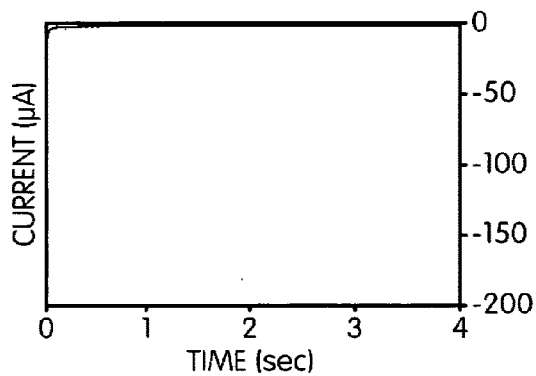
Figure 10E:
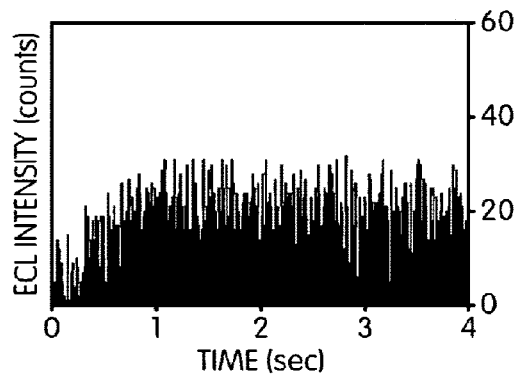
Figure 10C:
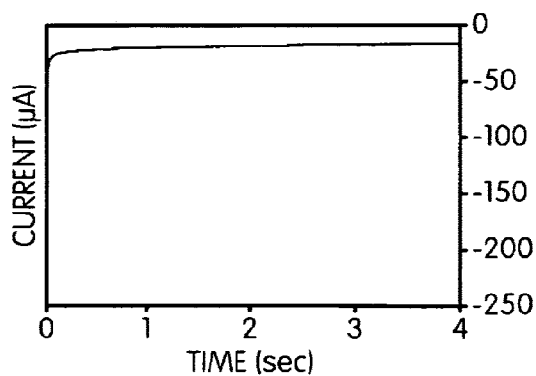
Figure 10F:
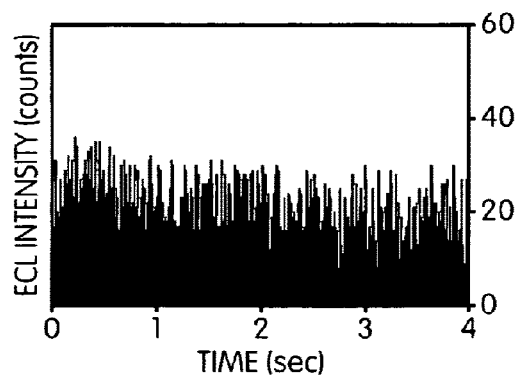
Figure 11A:
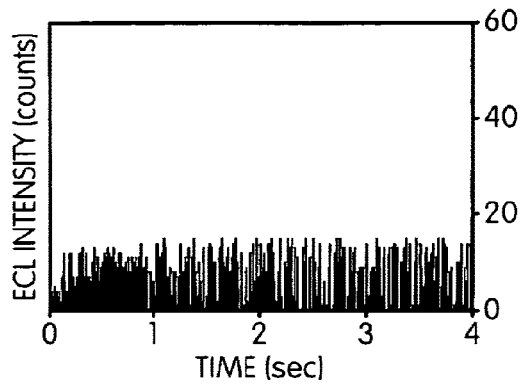
FIG. 11A (ECL+dark) counts=2222; Es=0.71
Figure 11D:
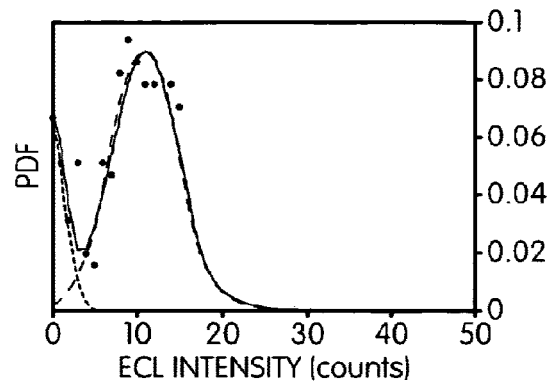
FIG. 11 shows the (ECL intensity vs. time) curves shown in FIG. 10 (FIG. 11A=FIG. 10D.
FIG. 11B=FIG. 10E.
FIG. 11C=FIG. 10F) and their corresponding PDFs (11D, 11E, and 11F, respectively) and the decomposed multi-Gaussian distributions.
Figure 11B:
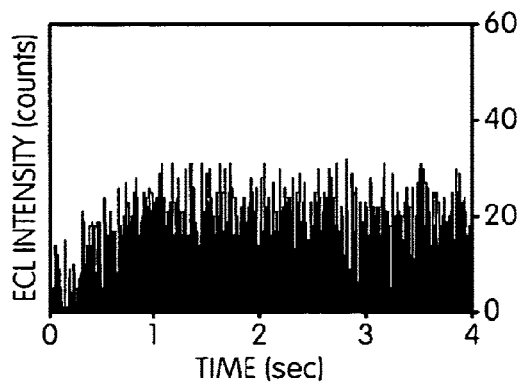
Figure 11E:
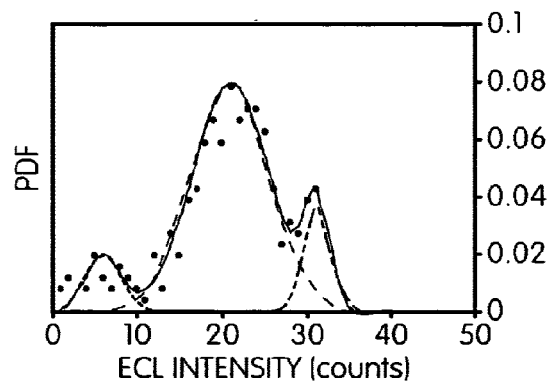
Figure 11C:
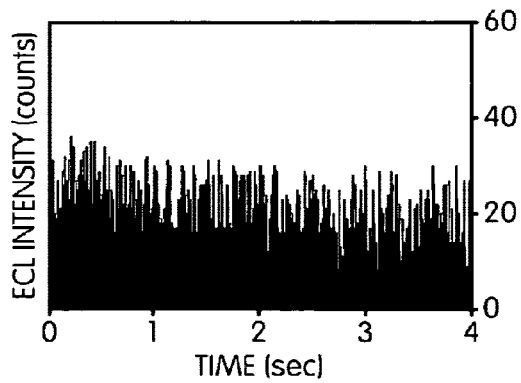
Figure 11F:
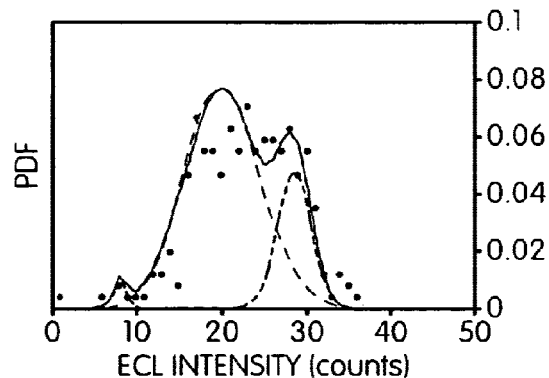

FIG. 6C shows the number of occurrences of the ECL event at an ITO electrode having same intensity, expressed as the probability density function ("PDF") for a (ECL intensity vs. time) record shown in FIG. 6A (total photon counts=8428) when no Pt NPs are present. Notice that the PDF shows a normal Gaussian distribution with an averaged ECL intensity peaked at ~33 counts. FIG. 6D shows the number of occurrences of the ECL event at an ITO electrode having same intensity, expressed as the probability density function ("PDF") for a (ECL intensity vs. time) record shown in FIG. 6B (total photon counts=9968) when ~2 nM Pt NPs are present. The ITO potential was stepped from 0 to 0.91 V vs. SCE for a duration of 4 seconds.

FIG. 7 shows the (ECL intensity vs. times) curves (7A (total photon counts=8428), 7B (total photon counts=9217) and 7C (total photon counts=9968)) and the corresponding PDFs (7D, 7E, and 7F respectively) and their decomposed Gaussian distributions at the ITO electrode at three difference colloidal Pt NP concentrations (0 nM Pt NPs (7A and 7D); ~1 nM Pt NPs (7B and 7E); and ~2 nM Pt NPs (7C and 7F)) but at nearly the same concentrations of the indicator species and coreactant. As shown, the overall ECL intensity increased by ~10% for each increment of ~1 nM Pt NPs added. Besides the major PDF peak at ~33 counts observed in the absence of Pt NPs, multi peaks develop as the concentration of Pt NPs increases, e.g., peaks near 20 and 46 counts for the curve shown in FIG. 7E. The relative contribution to the overall ECL intensity of the peak near 46 counts increases with increasing NP concentration, suggesting that this peak is mainly contributed from NP collisions. Note that the position of the ECL peak near 34 counts depends only slightly on the NP concentration.

FIG. 8 shows different (ECL intensity vs. time) records resulting from different concentrations of the indicator species by keeping the concentrations of Pt NPs and coreactant nearly constant. As shown, overall ECL intensity increases with increasing concentration of the indicator species, e.g., $Ru(bpy)_3^{2+}$ in this case. The fluctuation in the ECL intensity over the continuous ECL background also increases with increasing concentration of the indicator species. This behavior reflects well in the corresponding PDFs shown in FIG. 9, which shows not only the distribution but also the relative amplitude of the PDFs are strongly dependent on the concentration of the indicator species.

Each current and ECL profile is associated with individual single molecule and NP collisions on the measuring electrode. The characteristics of an individual (ECL intensity vs. time) profile are affected by the particle size, the particle residence time, the interaction between particle and the electrode surface, the life times of the active intermediates of the indicator species and coreactant and the kinetics for the generation of the excited state of the indicator species. In most case, a particle leaves the electrode after its collision so the ECL intensity increases very sharply by showing a big photon spike but then returns to the continuous ECL background.

FIG. 10 illustrates the current transients and the corresponding (ECL intensity vs. time) curves at an ITO electrode at different applied potentials. In the kinetic-controlled region (potential well negative of peak potential in the cyclic voltammograms or (ECL intensity vs. potential) curves shown in FIG. 4), both overall ECL intensity and ECL intensity fluctuation increase with increasing bias (see e.g., FIGS. 10D and E). There is also an attractive interaction between the negatively charged particle and the positively charged surface (the electrophoretic effect), causing the particles to stick on the electrode surface. We have examined this effect by setting the potential at even more positive values. We observed more collisions (see FIG. 10F), although mass transfer and kinetic limitations are involved.

The (ECL intensity vs. time) curves and the corresponding PDFs at different step potentials are shown in FIG. 11. The fluctuations in the ECL intensity are characteristics of multi normal distributions as shown in FIGS. 11D, E and F. The reason that the ECL generated in each individual collision events fluctuates is due to the random nature of the NP transport and collision to the electrode surface (e.g. how closely a particle can approach to the electrode surface within a distance where electron tunneling is possible), the residence time, and also to particle size effects.

Figure 12A:
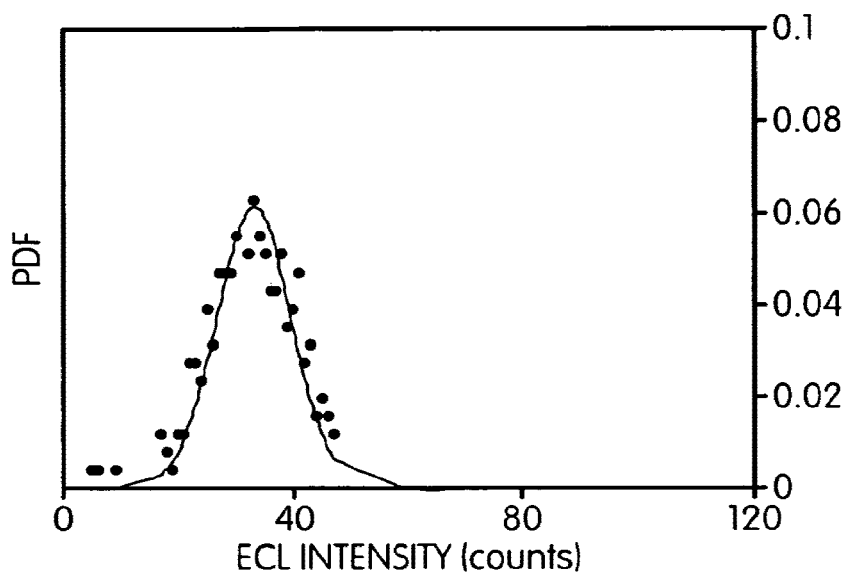
In FIG. 12A, Es=0.91 V vs. SCE; mean, μ=33 counts; and variance, σ=6.5.
Figure 12B:
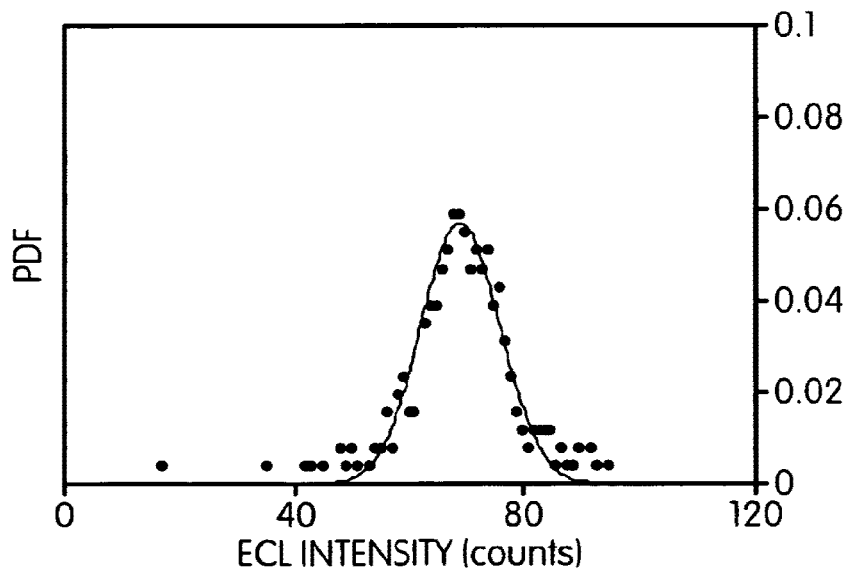
In FIG. 12B, Es=0.91 V vs. SCE; μ=69 counts; and σ=7.
Figure 13A:
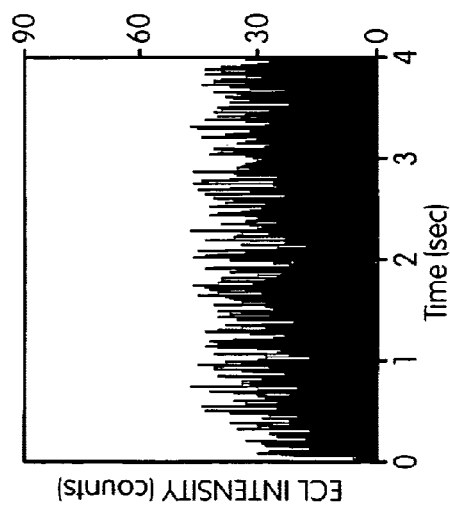
FIG. 13A total photon counts=8428.
Figure 13B:
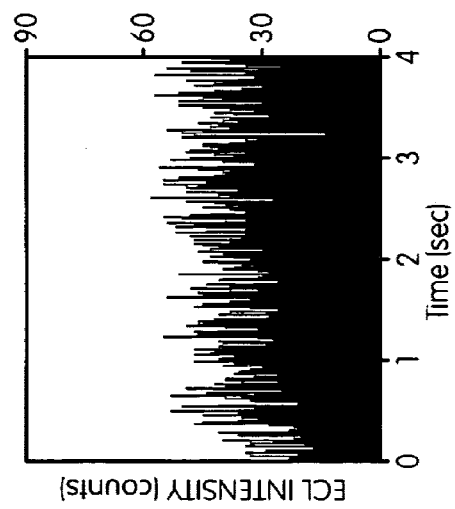
FIG. 13B=FIG. 7C), illustrating the fluctuation of ECL intensity in the frequency domain caused by Pt NPs. Es=0.91 V vs. SCE for FIGS. 13A-13D. For FIG. 13D, MCS dwt=15.6 ms.
Figure 13C:
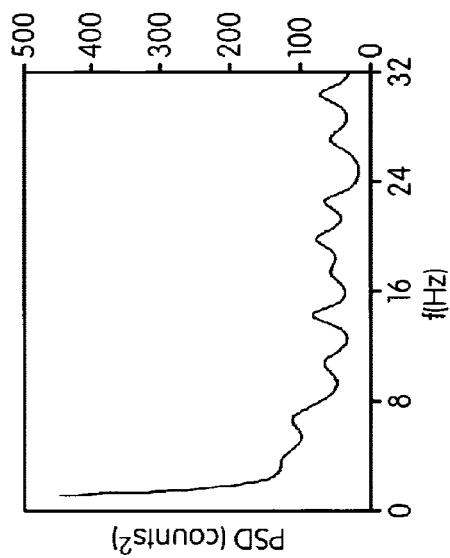
FIG. 13 shows examples of spectral density functions ("SDFs") (13C and 13D) of the ECL transients (13A and 13B) resulting from two different colloidal Pt NP concentrations (0 nm Pt NPs (13A and 13C); ~2 nM Pt NPs (13B and 13D)) as shown in FIG. 7 (FIG. 13A=FIG. 7A.
Figure 13D:
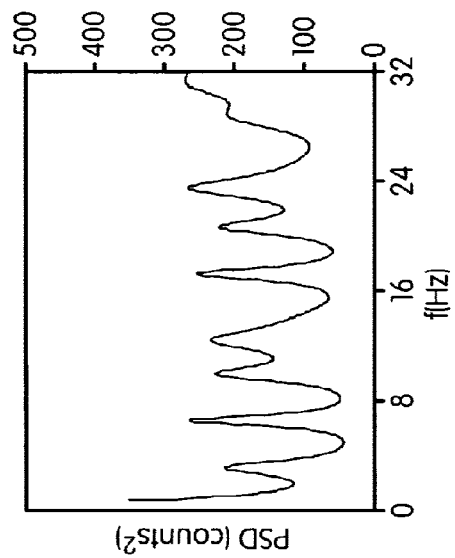

For comparison, the ECL transients and the corresponding PDFs resulting from different concentrations of the indicator species in the absence of Pt NPs are evaluated (see FIG. 12). As shown, the PDFs show predominantly single normal distributions with the average ECL intensity nearly proportional to the concentration of the indicator species.

FIG. 13 compares spectral density functions ("SDFs") of the ECL transients in a solution containing or without containing colloidal Pt NPs. SDFs of the ECL transients express the fluctuation of ECL intensity in the frequency domain. As shown, in a solution with or without Pt NPs, a large portion of the overall ECL intensity is contributed from the nearly steady-state (f=0 Hz) continuous background. The presence of Pt NPs in the solution contributes significantly those ECL intensity fluctuations of various low frequency components (f≥3 Hz), suggesting the polydispersity of the NPs examined.

Figure 14:
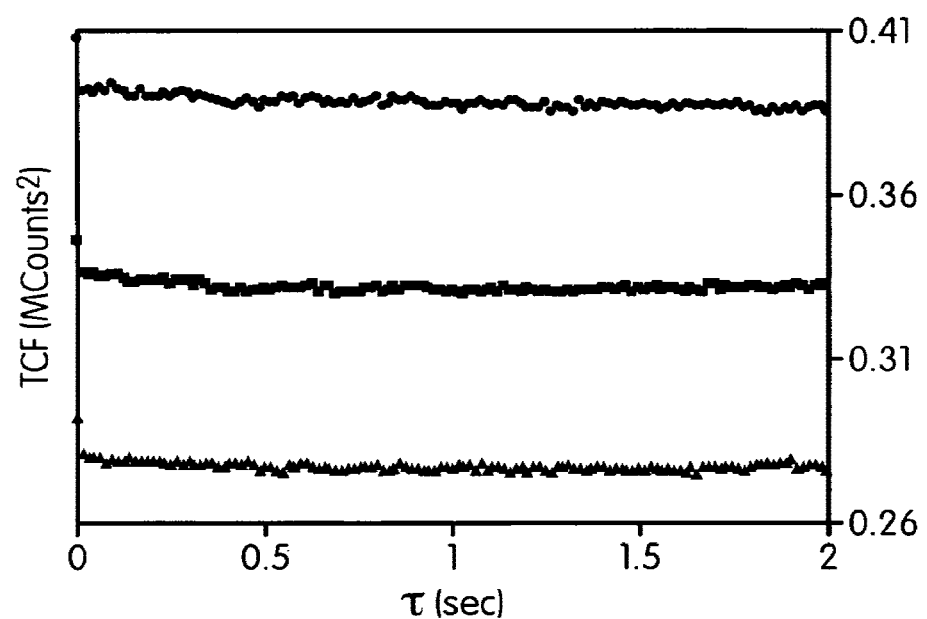
FIG. 14 illustrates examples of time correlation functions ("TCFs") of the ECL transients resulting from three different colloidal Pt NP concentrations (bottom function 0 nM Pt NPs; middle function ~1 nM Pt NPs; top function ~2 NM Pt NPs) as shown in FIG. 7.

The time correlation functions (TCFs) of several (ECL intensity vs. time) records as a function of the Pt NP concentrations (see FIG. 14) show the ECL intensity decays within ms to reach nearly steady-state values. The temporal response of ECL involved in a rapid EC reaction of a species (an/or its coreactant) in single particle collision events could reach the diffusion limit (a few ns) and allows us to study fast kinetics.

FIG. 15 shows the current and ECL intensity transients at an ITO electrode in a solution before and after injecting Pt NPs. As shown in FIGS. 15A and 15C, as long as a macro ITO electrode is used as the measuring electrode, the current transients are smoothly decaying curves, whether or not Pt NPs are present. However, the (ECL intensity vs. time) curves show significant fluctuations in the amplitude and frequency of photon counts (see FIGS. 15B and 15D). When the concentrations of the indicator species and coreactant are kept nearly constant, the fluctuations in photon counts depend strongly on the concentration of Pt NPs in the solution suggesting that they are associated with the catalyzed reactions on NPs as they collide with the supporting electrode.

Single NP collision events have been examined using $Ru(bpy)_3^{2+}$ as the indicator and TPrA as the coreactant, the skilled artisan will know that other indicators and/or coreactants may be used. In order to reduce the background current and enhance the relative ECL efficiency, an electrode or the NPs can undergo certain surface treatments. For example, a gold electrode can be coated with a surface assembled monolayer of benzenedimethanethiol, which forms a stable monolayer capable of electron tunneling to solution species. The other thiol group can strongly bind to the platinum particles. The macroelectrode or UME may include ITO, gold, nickel, Pt, Ir, Rh, and/or carbon (e.g., glassy carbon, graphite or diamond). In addition, the indicators species may be Ru $(bpy)_3^{2+}$ or other materials known to the skilled artisan.

Figure 16:
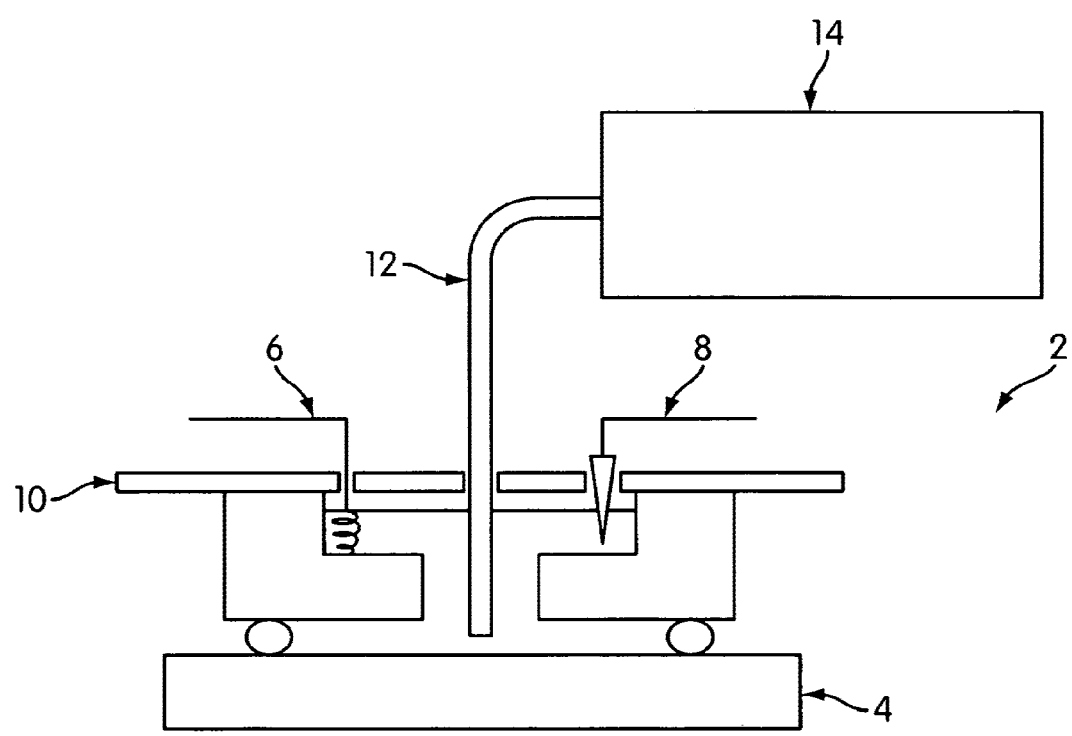
FIG. 16 depicts an illustrative embodiment of an electrochemical cell and the arrangement of the ITO electrode and optical system which can be employed in the present methods described herein. The exemplary cell includes an ITO working electrode, counter electrode, and reference electrode as well as a photon multiplier coupled to the sample cell through a photomultiplier tube.

FIG. 16 depicts a schematic of an exemplary electrochemical cell 2 which may be employed in the present method. The cell includes an ITO working electrode 4 and an optical system, which includes a photon detector 14. In the cell depicted in FIG. 16, no focusing lenses are placed between the ITO electrode and the input slit of the photon detector, which may be an avalanche style photodiode. The cell depicted in this figure also includes a counter electrode 6, which may be a platinum counter electrode, a reference electrode 8, such as a Ag/AgCl reference electrode, and a cover 10. In one embodiment, the cell includes an optical system, which includes an optical fiber 10; e.g., an optical fiber having a diameter of about 1 to 2 mm, connecting the photon detector 14 with the electrochemical cell 2. Suitable avalanche style photodiode may have an active area of about 10e-5 to 10e-4 $cm^2$. The active area of the ITO working electrode may suitably be about 0.01 to 0.5 $cm^2$.

The present application provides a novel method of observing single particle collision events with macro electrode or an UME. A single event characterized by the current or ECL generated through the particle-catalyzed reaction of an indicator with or without a coreactant present in solution. Since the indicator can be selected to have a high concentration and high diffusion coefficient, significant amplification occurs. Every collision produces a unique current or ECL transient that can be correlated to the particle size, the particle residence time, and the particle interaction with the electrode surface. By modifying the particle concentration, particle size (e.g. platinum citrate NPs vs. platinum oxalate NPs), applied substrate potential, and the concentration of the indicator, it should be possible to use the i-t profiles or the (ECL intensity vs. time) curves to obtain information about the indicator reaction at a single particle. In comparison to amplifying optical, conductivity and mass signals using NPs, the catalytic current or ECL amplification in the present method allows observation of single particle collision events and through the i-t or the (ECL intensity vs. time) curves, the study of electrochemical kinetics at the single particle level. Moreover, it might be useful in determining particle size distributions and as a very sensitive electroanalytical method, perhaps to the single binding event level.

The platinum NP solution was prepared by combining 60 mL of a 2 mM aqueous $H_2PtCl_6$ solution with 3 mL of 50 mM aqueous sodium citrate solution, then under vigorous stirring, with 7 mL 120 mM aqueous $NaBH_4$ solution, was added dropwise. The resulting solution was kept stirring for another half hour. The skilled artisan will recognize that other NP solutions may similarly be prepared, e.g., platinum, palladium and ruthenium.

The present application describes methods, compositions and kits for analyzing a chemical analyte having an electrochemical cell connected to a measuring apparatus. The electrochemical cell contains a solution having one or more conductive or redox active NPs, generally in the form of a colloidal solution of the NPs, one or more chemical analytes (as indicator and a coreactant). In addition, the electrochemical cell contains one or more electrodes in communication with the solution. One or more electrocatalytic properties are generated by the interaction of the one or more conductive or redox active NPs and the liquid sample and can be measured using one or more electrodes or other detection devices, e.g., a photon detector to measure emitted electromagnetic radiation.

The present application provides a method which includes the use of one or more conductive or redox active NPs in solution within the electrochemical cell. The conductive NPs may be entirely or partially metal. For example, the one or more conductive NPs may be platinum NPs, gold NPs, palladium NPs, carbon NPs, ITO NPs or mixtures and combinations thereof. The NPs may also have cores of a different material than the outer material of the NP. Although, the NPs may be of in diameter sized between about 0.5 nm and about 100 nm, a common size range for one embodiment is between about 1 nm and 10 nm in diameter and an average of 4 nm in diameter. Furthermore, the size distribution of NP diameter may be generally uniform, disperse, or varying. The NPs may have different groups of particles that have generally the same diameter within the group but differing diameter relative to the other groups in the solution.

The one or more electrocatalytic properties can be any property that can be measured by the apparatus; however the most common property is an electrocatalytic ECL amplification from a redox reaction catalyzed by conductive NPs. Examples of other suitable properties include a current, a resistance, an impedance, a capacitance, an inductance or a combination thereof.

Illustrative Embodiments

In one embodiment, a method of analyzing a sample is provided. The method includes adding one or more conductive or redox active NPs to a liquid sample within a sample chamber; and observing one or more electrochemical and/or optical properties generated by the interaction of the NPs and the liquid sample at an electrode. Measuring one or more electrochemical and/or optical properties may include measuring electrochemiluminescence intensity resulting from a redox reaction catalyzed by the nanoparticles. In some embodiments, the measurement may include measuring current amplification from a redox reaction catalyzed by the nanoparticles. Other electrocatalytic properties, which may be measured as part of such methods, include current, a resistance, an impedance, a capacitance, an inductance or a combination thereof. In many instances where the optical properties being measured include measuring electrochemiluminescence intensity, the sample further comprise an ECL coreactant, e.g., a tertiary amine such as a trialkyl amine.

Examples of suitable conductive nanoparticles which may be employed in the present methods include comprise platinum NPs, gold NPs, silver NPs, copper NPs, palladium NPs, carbon NPs, ITO NPs, conductive oxide NPs, conductive polymer NPs or a combination thereof. The nanoparticles employed in the present methods often have a largest dimension of no more than about 50 nm (e.g., a largest dimension of about 1 nm to 25 nm). For example, the nanoparticles may be about 1 nm to 10 nm in diameter (e.g., nanoparticles averaging about 4-5 nm in diameter).

Examples of suitable electrode materials for use in the present methods include ITO, Pt, Au, Ni, Rh, Ir and carbon (e.g., glassy carbon, graphite, or diamond). As exemplified in the present application, platinum NPs may be employed in methods which make use of a sample cell, e.g., a cell containing an indium tin oxide ("ITO") or gold working electrode.

Suitable ECL moieties employed in the present methods may comprise a redox active, ionic luminescent compound. For example, the redox active, ionic luminescent compound may include an electrochemiluminescent polydendate metal complex, e.g., a polydendate metal complex which includes one or more heteroaromatic polydentate ligands and a metal chosen from ruthenium, osmium, rhenium, cerium, europium, terbium and ytterbium. The polydendate metal complex may comprise ruthenium and at least one polydentate ligand selected from bipyridyl, substituted bipyridyl, 1,10-phenanthroline and/or substituted 1,10-phenanthroline.

Another embodiment is directed to a kit for analyzing a chemical analyte. The kit includes:
  one or more conductive or redox active NPs;
  one or more chemical indicators, such as an ECL label; and
  one or more electrodes located within a sample chamber, such as a flow cell.

The electrochemical cell is connectable to a measuring apparatus. The conductive or redox active NPs, the chemical analyte and at least one electrode are in communication with a solution so as to generate electrocatalytic current and/or ECL properties which are readable by the measuring apparatus.

Another embodiment provides a method of analyzing a sample including (a) adding one or more nanoparticles to a liquid sample in a chamber and (b) measuring one or more electrochemical and/or optical properties resulting from interaction of the one or more nanoparticles and the sample at an electrode. The sample chamber has one or more electrodes located therein, e.g., may include a working electrode, a counter electrode and a reference electrode. The sample includes a plurality of moieties capable of electrogenerated chemiluminescent ("ECL moieties") and often will also include a co-reactant that can enhance the electrogenerated chemiluminescence of the ECL moieties. For example, when the sample include a plurality of ruthenium based ECL moieties, it may be advantageous to include a tertiary alkyl amine, such as tripropyl amine ("TPrA"), as a co-reactant in the sample. The nanoparticles are formed from conductive or redox active material. Examples of suitable conductive nanoparticles which may be employed in this embodiment include platinum NPs, gold NPs, silver NPs, copper NPs, palladium NPs, carbon NPs, and/or conductive oxide NPs.

Another embodiment provides a method of analyzing a sample including (a) adding one or more conductive nanoparticles to a liquid sample in a chamber and (b) measuring one or more electrochemical and/or optical properties resulting from interaction of the one or more nanoparticles and the sample at an electrode. Examples of suitable conductive nanoparticles include comprise platinum NPs, gold NPs, silver NPs, copper NPs, palladium NPs, carbon NPs, ITO NPs, conductive oxide NPs, conductive NPs or a combination thereof. As exemplified in the present application, platinum NPs may be employed in such methods which make use of a sample cell containing an indium tin oxide working electrode. In this embodiment, measuring the electrochemical and/or optical properties may comprises measuring electrochemiluminescence intensity resulting from a redox reaction catalyzed by the nanoparticles. In some embodiments, the measurement may include measuring current amplification from a redox reaction catalyzed by the nanoparticles.

Other embodiments provide a device for analyzing a chemical analyte having at least one nanoparticle. The device suitably includes an electrochemical cell connected to a measuring apparatus. The electrochemical cell is capable of containing a solution comprising one or more conductive or redox active NPs, one or more chemical analytes, an indicator and has one or more electrodes in communication with the solution. The device is capable of measuring one or more electrochemical properties are generated by the interaction of the NPs and the liquid sample at one or more electrodes.

Another embodiment is directed to method of signal amplification which includes (a) combining one or more conductive or redox active NPs and a sample in a chamber having one or more electrodes; and (b) measuring one or more electrochemical properties generated by the interaction of the NPs and the sample at the one of the electrodes.

Another embodiment provides a method of signal amplification comprising the steps of:

combining one or more conductive or redox active NPs and a sample in a chamber having one or more electrodes; and measuring one or more electrochemical and/or optical properties generated by the interaction of the one or more conductive or redox active NPs and the sample at the one or more electrodes. The one or more electrochemical and/or optical properties may comprise electrogenerated chemiluminescence from a redox reaction catalyzed by the one or more NPs. The one or more electrochemical and/or optical properties may comprise current amplification from a redox reaction catalyzed by the one or more NPs, e.g., a redox reaction involving an ECL moiety and, optionally, an ECL coreactant such as a trialkyl amine (e.g., tripropylamine).

The present application provides a method and apparatus, which may be used for observing the ECL generated during collisions of single NPs at an electrode. The method and apparatus can provide information of electrochemical processes at single NPs, as well as the basis of highly sensitive electroanalytical methods. Such methods typically include contacting a liquid sample, which is a colloidal solution of conductive or redox active nanoparticles, with one or more electrodes in a sample chamber; and observing at least one electrochemical and/or optical property generated by the interaction of the NPs and the liquid sample at an electrode. The liquid sample typically includes a compound capable of ECL (an "ECL label compound") and optionally, an ECL coreactant, such as a tertiary alkyl amine, e.g., tripropyl amine. The sample solutions commonly contain much higher concentrations of the ECL label compound and optional coreactant. For example, when the concentration of the colloidal NPs is in the pM to nM range, the sample solution may include about 1 to 20 μM of an ECL label compound, e.g., an Ru(bpy)$_3^{2+}$ salt, and about 1 to 100 mM of a ECL coreactant, such as tripropyl amine. In some embodiments, the measurement may include measuring current amplification from a redox reaction catalyzed by the nanoparticles. In certain embodiments, the measurement may include measuring electrochemiluminescence intensity resulting from a redox reaction catalyzed by the nanoparticles. Other electrocatalytic properties which may be measured as part of such methods include current, resistance, impedance, capacitance, inductance or a combination thereof.

Another embodiment is directed to a nanoscale electrochemical cell to analyze a sample containing at least one NP where the nanoscale cell comprises:

one or more electrodes positioned to communicate with a sample housed within a sample chamber;

one or more conductive or redox active NPs deposited within the sample chamber, wherein the one or more conductive or redox active NPs interact with the sample to generate one or more electrocatalytic current or ECL properties; and detectors in communication with the one or more electrodes to detect the one or more electrocatalytic current or ECL properties. The nanoscale electrochemical cell may comprise an UME or macroelectrode (i.e., be positioned so that a sample compartment is in contact with the macroelectrode). The NPs may comprise platinum NPs, gold NPs, silver NPs, copper NPs, palladium NPs, carbon NPs, ITO NPs, conductive oxide NPs, conductive or redox polymer NPs or a combination thereof.

In another embodiment, the method of analyzing a sample comprises: introducing one or more conductive or redox active nanoparticles and a liquid sample into a chamber having one or more electrodes, wherein the sample comprises a plurality of electrogenerated chemiluminescent ('ECL') moieties; and measuring one or more electrochemical and/or optical properties resulting from electrocatalytic interaction of the one or more nanoparticles and the sample at the one or more electrodes. The sample may further comprise an ECL coreactant, such as a aliphatic tertiary amine, e.g., tripropyl amine or triethyl amine. The ECL moieties may comprise a ruthenium-containing organic compound. The one or more conductive or redox active nanoparticles may comprise platinum nanoparticles, e.g., where the electrodes include an indium tin oxide working electrode. Measuring one or more electrochemical and/or optical properties may comprise measuring current amplification from a redox reaction catalyzed by the one or more conductive or redox active nanoparticles and/or may comprise measuring electrochemiluminescence intensity resulting from a redox reaction catalyzed by the one or more conductive or redox active nanoparticles.

It is contemplated that any embodiments discussed in this specification may be implemented with respect to any method, kit, reagent, or composition as described herein, and vice versa. Furthermore, the present compositions can be used to achieve methods described herein.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

The use of the word "a" or "an" when in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claims(s), the worlds "comprising" (and any form of comprising, such as "comprise" and "comprises"), "having" (and any for of having, such as "have" and "has"), "including" (and any form of including, such as "includes" and "include") or "containing" (and any form of containing, such as "contains" and "contain") are inclusive ore open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in particular context, also BA, CA, CB, BCA, BCA, ACB, BAC, or CAB. Continuing with this example, expressly included are combinations that contain repeats of one or more item or term, such as BB, AAA, MB, BBC, AAABCCCC, BCCAAA, CABABB, and so forth. The skilled artisan will understand typically there is not limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of certain exemplary embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention.

What is claimed is:

1. A method of signal amplification comprising:
    contacting a colloidal suspension of conductive nanoparticles in a liquid sample with a working electrode; wherein the liquid sample comprises a plurality of electrogenerated chemiluminescent (ECL) moieties and one or more analytes; and
    detecting an ECL intensity vs. time transient of optical emissions by the ECL moieties resulting from redox reactions of the ECL moieties, with or without coreactants, wherein the ECL intensity vs. time transient is generated by a collision of a single nanoparticle with the working electrode.

2. The method of claim 1, wherein the working electrode comprises indium tin oxide (ITO), Pt, Ir, Rh, Au, carbon, Ni or a combination thereof.

3. The method of claim 1, wherein the conductive nanoparticles comprise platinum nanoparticles, gold nanoparticles, silver nanoparticles, copper nanoparticles, palladium nanoparticles, ruthenium nanoparticles, carbon nanoparticles, or a combination thereof.

4. The method of claim 1, wherein the nanoparticles have a largest dimension of no more than about 50 nm.

5. The method of claim 1, wherein the nanoparticles comprise platinum nanoparticles; and the working electrode is an ITO working electrode.

6. The method of claim 1, wherein the sample further comprises an ECL coreactant.

7. The method of claim 1, wherein the working electrode is at a potential which does not produce electrogenerated chemiluminescence in the absence of the nanoparticles.

8. The method of claim 1, wherein the ECL moieties are capable of repeatedly undergoing one or more chemical reactions to produce species which electrochemiluminesce.

9. The method of claim 1, wherein the nanoparticles are conductive metal nanoparticles, conductive oxide nanoparticles, conductive polymer nanoparticles, conductive carbon nanoparticles or a combination thereof.

10. The method of claim 1, wherein the ECL moieties comprise an electrochemiluminescent polydendate metal complex.

11. The method of claim 10, wherein the polydendate metal complex comprises heteroaromatic polydentate ligands and a metal chosen from ruthenium, osmium, rhenium, cerium, europium, terbium and ytterbium.

12. The method of claim 10, wherein the polydendate metal complex comprises ruthenium and at least one polydentate ligand selected from bipyridyl, substituted bipyridyl, 1,10-phenanthroline and substituted 1,10-phenanthroline.

13. The method of claim 10, wherein the working electrode comprises Pt, Au, Ir, Rh, carbon or a combination thereof.

14. The method of claim 10, wherein the working electrode is an indium tin oxide electrode, the nanoparticles are platinum nanoparticles, and the working electrode surface is at a potential which does not produce electrogenerated chemiluminescent in the absence of the nanoparticles.

15. The method of claim 10, wherein the liquid sample further comprises an ECL coreactant comprising trialkyl amine.

16. The method of claim 1, wherein the nanoparticles comprise platinum or palladium nanoparticles having a largest dimension of no more than about 50 nm; the working electrode is an indium tin oxide electrode; each of the ECL moieties comprise an electrochemiluminescent polydendate ruthenium complex; and the liquid sample further comprises an ECL coreactant which includes trialkyl amine.

17. The method of claim 16, wherein the nanoparticles comprise platinum nanoparticles; the ECL coreactant comprises triethyl amine; and the electrochemiluminescent polydendate metal complex comprises $Ru(bpy)_3^{2+}$.

18. The method of claim 1, wherein the working electrode is an ultramicroelectrode.

19. The method of claim 1, wherein the ECL moieties each comprise a polydendate ruthenium complex which includes heteroaromatic polydentate ligands; and the sample further comprises a trialkyl amine ECL coreactant.

20. The method of claim 19, wherein the working electrode is an indium tin oxide ultramicroelectrode, the nanoparticles are platinum nanoparticles, and the working electrode surface is at a potential which does not produce electrogenerated chemiluminescent in the absence of the platinum nanoparticles.

* * * * *